(12) United States Patent
Haines et al.

(10) Patent No.: US 8,158,344 B2
(45) Date of Patent: Apr. 17, 2012

(54) METHODS AND COMPOSITIONS FOR CORRELATING GENETIC MARKERS WITH MULTIPLE SCLEROSIS

(75) Inventors: Jonathan L. Haines, Nashville, TN (US); Simon G. Gregory, Durham, NC (US); Silke Schmidt, Durham, NC (US); Margaret A. Pericak-Vance, Coral Gables, FL (US); Mariano Garcia-Blanco, Durham, NC (US)

(73) Assignees: Duke University, Durham, NC (US); Vanderbilt University, Nashville, TN (US)

( * ) Notice: Subject to any disclaimer, the term of this patent is extended or adjusted under 35 U.S.C. 154(b) by 292 days.

(21) Appl. No.: 12/147,171

(22) Filed: Jun. 26, 2008

(65) Prior Publication Data

US 2009/0035778 A1 Feb. 5, 2009

Related U.S. Application Data

(60) Provisional application No. 60/937,811, filed on Jun. 29, 2007.

(51) Int. Cl.
*C12Q 1/68* (2006.01)
*C07H 21/02* (2006.01)
*C07H 21/04* (2006.01)

(52) U.S. Cl. .......................... 435/6; 536/24.3; 536/24.1

(58) Field of Classification Search .................. None
See application file for complete search history.

(56) References Cited

OTHER PUBLICATIONS

Ramanathan et al (Journal of Neuroimmunology 2001 vol. 116 p. 213).*
Booth et al. (Journal of Molecular Medicine 2005 vol. 83 p. 822).*
Sharief et al. (J Neurol Neurosug Psychiatry 1993 vol. 56 p. 169).*
Padberg et al. (Journal of Neuroimmunology 1999 vol. 99 p. 218).*
Enard et al. (Science 2002 vol. 296 p. 340).*
Cobb et al (Crit Care Med 2002 vol. 30 p. 2711).*
Akkad et al. (Journal of Autoimmunity 2009 vol. 32 p. 110).*
Rane et al. (Journal of Neuroimmunology 2010 vol. 222 p. 82).*
Brassat et al. "Multifactor Dimensionality Reduction Reveals Gene-Gene Interactions Associated with Multiple Sclerosis Susceptibility in African Americans" *Genes and Immunity* 7:310-315 (2006).
Carstens et al. "An Intronic Sequence Element Mediates Both Activation and Repression of Rat Fibroblast Growth Factor Receptor 2 Pre-mRNA Splicing" *Molecular and Cellular Biology* 18(4):2205-2217 (1998).
GenBank Accession No. NM_002185. *Homo sapiens* interleukin 7 receptor (IL7R), mRNA. Jun. 26, 2007 (4 pages).
GenBank Accession No. NP_002176. Interleukin 7 receptor precursor [*Homo sapiens*]. Jun. 26, 2007 (4 pages).
Gregory et al. "Interleukin 7 Receptor α Chain (IL7R) Shows Allelic and Functional Association with Multiple Sclerosis" *Nature Genetics* 39(9):1083-1091 (2007).
Gregory et al. "Allelic Association of the Interleukin 7 Receptor Gene (IL7R) with Multiple Sclerosis (MS)" Abstract for The American Society of Human Genetics meeting in New Orleans, LA in Oct. 2006 (Aug. 2006) (1 page).
Gregory et al. "Allelic Association of the Interleukin Receptor Gene (IL7R) with Multiple Sclerosis" Slides for presentation at The American Society of Human Genetics meeting in New Orleans, LA (Oct. 11, 2006) (10 pages).
Hafler et al. "Risk Alleles for Multiple Sclerosis Identified by a Genomewide Study" *The New England Journal of Medicine* 357(9):851-862 (2007).
Kenealy et al. "Examination of Seven Candidate Regions for Multiple Sclerosis: Strong Evidence of Linkage to Chromosome 1q44" *Genes and Immunity* 7:73-76 (2006).
Lundmark et al. "Variation in Interleukin 7 Receptor α Chain (IL7R) Influences Risk of Multiple Sclerosis" *Nature Genetics* 39(9):1108-1113 (2007).
McCauley et al. "SNPs in Multi-Species Conserved Sequences (MCS) as Useful Markers in Association Studies: a Practical Approach" *BMC Genomics*, 8:266 (2007).
Motsinger et al. "Complex Gene-Gene Interactions in Multiple Sclerosis: a Multifactorial Approach Reveals Associations with Inflammatory Genes" *Neurogenetics* 8:11-20 (2007).
Sawcer et al. "A High-Density Screen for Linkage in Multiple Sclerosis" *Am J Hum Genet* 77:454-467 (2005).
Schmidt et al. "Allelic Association of Sequence Variants in the Herpes Virus Entry Mediator-B Gene (PVRL2) with the Severity of Multiple Sclerosis" *Genes and Immunity* 7:384-392 (2006).
Single Nucleotide Polymorphism (SNP) RefSNP ID: rs6897932; NCBI Assay ID No. ss44625331, Jun. 27, 2003 (4 pages).
Teutsch et al. "Identification of 11 Novel and Common Single Nucleotide Polymorphisms in the Interleukin-7 Receptor-α Gene and Their Associations with Multiple Sclerosis" *European Journal of Human Genetics* 11:509-515 (2003).
Yeo et al. "A Second Major Histocompatibility Complex Susceptibility Locus for Multiple Sclerosis" *Ann Neurol* 61:228-236 (2007).
Zhang et al. "Two Genes Encoding Immune-Regulatory Molecules (LAG3 and IL7R) Confer Susceptibility to Multiple Sclerosis" *Genes and Immunity* 6:145-152 (2005).
Zuvich et al. "Genetic Variation in the IL7RA/IL7 Pathway Increases Multiple Sclerosis Susceptibility" *Hum Genet* 127:525-535 (2010).

\* cited by examiner

*Primary Examiner* — Katherine Salmon
(74) *Attorney, Agent, or Firm* — Myers Bigel Sibley & Sajovec, P.A.

(57) ABSTRACT

The present invention provides, in certain aspects, a method of identifying a subject as having an increased risk of developing multiple sclerosis, comprising detecting in the subject the presence of a nucleotide variant in the interleukin 7 receptor alpha chain gene, whereby the presence of said variant identifies the subject as having an increased risk of developing multiple sclerosis.

6 Claims, 3 Drawing Sheets

US 8,158,344 B2

METHODS AND COMPOSITIONS FOR CORRELATING GENETIC MARKERS WITH MULTIPLE SCLEROSIS

STATEMENT OF PRIORITY

This application claims the benefit, under 35 U.S.C. §119 (e), of U.S. Provisional Application No. 60/937,811, filed Jun. 29, 2007, the entire contents of which are incorporated by reference herein.

GOVERNMENT SUPPORT

Aspects of the present invention were made with the support of federal grant number NS032830 from the National Institutes of Health/National Institute of Neurological Disorders and Stroke. The United States Government has certain rights to this invention.

FIELD OF THE INVENTION

The present invention provides methods and compositions directed to identification of genetic markers associated with multiple sclerosis.

BACKGROUND OF THE INVENTION

Multiple sclerosis (MS) is a genetic disease caused by demyelination of nerve tissue, which leads to cognitive deficits, balance and coordination impairment, pain and numbness, amongst other clinical presentation. MS is the prototypic human demyelinating disease with evidence from numerous epidemiologic, adoption and twin studies for a strong underlying genetic liability (Wilier et al. (2003)*Proc. Natl. Acad. Sci. U.S.A* 100:12877-12882). The disease is most common in young adults, with more than 90% of patients diagnosed before the age of 55 and less than 5% before the age of 14. Females are 2-3 times more frequently affected than males (Fernald et al. (2005) *J. Neuroimmunol.* 167:157-169) and the disease course can vary substantially with some patients suffering only minor disability several decades after their initial diagnosis, and others reaching wheelchair dependency shortly after disease onset.

To identify genetic contributions that underlie the development and progression of MS, several different approaches, including genetic linkage, candidate gene association and gene expression studies have been independently employed (Fernald et al. (2005) *J. Neuroimmunol.* 167:157-169). However, the genetic linkage screens have failed to consistently identify consensus regions outside of the HLA class II locus. Candidate gene studies have suggested over 100 different associated genes, but none have reached consensus. Similarly, gene expression studies have identified hundreds of differentially expressed transcripts with little consistency across studies.

The present invention overcomes previous shortcomings in the art by employing genomic convergence (Hauser et al. (2003) *Hum. Mol. Genet.* 12:671-677), which takes advantage of the strengths of each method by combining evidence from both statistical and functional data, to identify significant statistical associations between nucleotide variants within the interleukin 7 receptor alpha (IL7Rα) chain gene and MS.

SUMMARY OF THE INVENTION

Thus, in one aspect, the present invention provides a method of identifying a subject as having an increased risk of developing multiple sclerosis or as having multiple sclerosis, comprising detecting in the subject the presence of a C allele of the single nucleotide polymorphism rs6897932 of the interleukin 7 receptor alpha chain gene, whereby the presence of said C allele identifies the subject as having an increased risk of developing multiple sclerosis or as having multiple sclerosis.

In a further aspect, the present invention provides a method of identifying a subject as having an increased risk of developing multiple sclerosis or as having multiple sclerosis, comprising detecting an increase in the amount of soluble interleukin 7 receptor alpha chain in the subject relative to the amount of soluble interleukin 7 receptor alpha chain in a control subject, whereby the increase in the amount of soluble interleukin 7 receptor alpha chain identifies the subject as having an increased risk of developing multiple sclerosis or as having multiple sclerosis.

Further aspects of this invention include a method of identifying a subject as having an increased risk of developing multiple sclerosis or as having multiple sclerosis, comprising detecting a decrease in the amount of membrane-bound interleukin 7 receptor alpha chain in the subject relative to the amount of membrane-bound interleukin 7 receptor alpha chain in a control subject, whereby the decrease in the amount of membrane-bound interleukin 7 receptor alpha chain identifies the subject as having an increased risk of developing multiple sclerosis or as having multiple sclerosis.

Furthermore, the present invention provides a method of identifying a subject as having an increased risk of developing multiple sclerosis or as having multiple sclerosis, comprising detecting an increase in the amount of interleukin 7 receptor alpha chain mRNA lacking exon 6 in the subject relative to the amount of interleukin 7 receptor alpha chain mRNA lacking exon 6 in a control subject, whereby the increase in the amount of interleukin 7 receptor alpha chain mRNA lacking exon 6 identifies the subject as having an increased risk of developing multiple sclerosis or as having multiple sclerosis.

In addition, the present invention provides a method of identifying a subject as having an increased risk of developing multiple sclerosis or as having multiple sclerosis, comprising detecting a decrease in the amount of interleukin 7 receptor alpha chain mRNA comprising exon 6 in the subject relative to the amount of interleukin 7 receptor alpha chain mRNA comprising exon 6 in a control subject, whereby the decrease in the amount of interleukin 7 receptor alpha chain mRNA comprising exon 6 identifies the subject as having an increased risk of developing multiple sclerosis or as having multiple sclerosis.

Further provided herein is a method of identifying a subject as having an increased risk of developing multiple sclerosis and/or as having multiple sclerosis, comprising detecting in the subject the presence, in the interleukin 7 receptor alpha chain gene, of a haplotype comprising the C allele of single nucleotide polymorphism rs6897932, and an allele selected from the group consisting of: a) the C allele of single nucleotide polymorphism rs1494555; b) the T allele of single nucleotide polymorphism rs1494555; c) the C allele of single nucleotide polymorphism rs987107; d) the T allele of single nucleotide polymorphism rs987107; e) the A allele of single nucleotide polymorphism rs987106; f) the T allele of single nucleotide polymorphism rs987106 and g) any combination of (a), (b), (c) (d), (e) and (f), whereby the presence of said haplotype identifies the subject as having an increased risk of developing multiple sclerosis.

In some embodiments the haplotype can comprise, consist essentially of and/or consist of a) the C allele of single nucleotide polymorphism rs6897932, b) the C allele of single nucleotide polymorphism rs1494555; c) the C allele of single nucleotide polymorphism rs987107; and d) the A allele of single nucleotide polymorphism rs987106.

In other embodiments, the haplotype can comprise, consist essentially or and/or consist of a) the C allele of single nucleotide polymorphism rs6897932, b) the T allele of single nucleotide polymorphism rs1494555; c) the T allele of single nucleotide polymorphism rs987107; and d) the T allele of single nucleotide polymorphism rs987106.

In further embodiments, the haplotype can comprise, consist essentially or and/or consist of a) the C allele of single nucleotide polymorphism rs6897932, b) the T allele of single nucleotide polymorphism rs1494555; c) the C allele of single nucleotide polymorphism rs987107; and d) the A allele of single nucleotide polymorphism rs987106.

Other aspects of the present invention include a method of identifying a subject as having a decreased risk of developing multiple sclerosis, comprising detecting in the subject the presence of a T allele of the single nucleotide polymorphism rs6897932 of the interleukin 7 receptor alpha chain gene, whereby the presence of said T allele identifies the subject as having a decreased risk of developing multiple sclerosis.

Further provided herein is a method of identifying a subject as having a decreased risk of developing multiple sclerosis, comprising detecting in the subject the presence, in the interleukin 7 receptor alpha chain gene, of a haplotype comprising: a) the T allele of the single nucleotide polymorphism rs6897932; b) the T allele of the single nucleotide polymorphism rs1494555; c) the C allele of the single nucleotide polymorphism rs987107; and d) the T allele of the single nucleotide polymorphism rs987106, whereby the presence of said haplotype identifies the subject as having a decreased risk of developing multiple sclerosis.

Also provided herein is a method of identifying a subject as having a decreased risk of developing multiple sclerosis, comprising detecting a decrease in the amount of soluble interleukin 7 receptor alpha chain in the subject relative to the amount of soluble interleukin 7 receptor alpha chain in a control subject, whereby the decrease in the amount of soluble interleukin 7 receptor alpha chain identifies the subject as having a decreased risk of developing multiple sclerosis.

Further provided is a method of identifying a subject as having a decreased risk of developing multiple sclerosis, comprising detecting an increase in the amount of membrane-bound interleukin 7 receptor alpha chain in the subject relative to the amount of membrane-bound interleukin 7 receptor alpha chain in a control subject, whereby the increase in the amount of membrane-bound interleukin 7 receptor alpha chain identifies the subject as having a decreased risk of developing multiple sclerosis.

In addition, the present invention provides a method of identifying a subject as having a decreased risk of developing multiple sclerosis, comprising detecting a decrease in the amount of interleukin 7 receptor alpha chain mRNA lacking exon 6 in the subject relative to the amount of interleukin 7 receptor alpha chain mRNA lacking exon 6 in a control subject, whereby the decrease in the amount of interleukin 7 receptor alpha chain mRNA lacking exon 6 identifies the subject as having a decreased risk of developing multiple sclerosis.

In additional aspects, the present invention provides a method of identifying a subject as having a decreased risk of developing multiple sclerosis, comprising detecting an increase in the amount of interleukin 7 receptor alpha chain mRNA comprising exon 6 in the subject relative to the amount of interleukin 7 receptor alpha chain mRNA comprising exon 6 in a control subject, whereby the increase in the amount of interleukin 7 receptor alpha chain mRNA comprising exon 6 identifies the subject as having a decreased risk of developing multiple sclerosis.

DETAILED DESCRIPTION OF THE INVENTION

Figure 1:
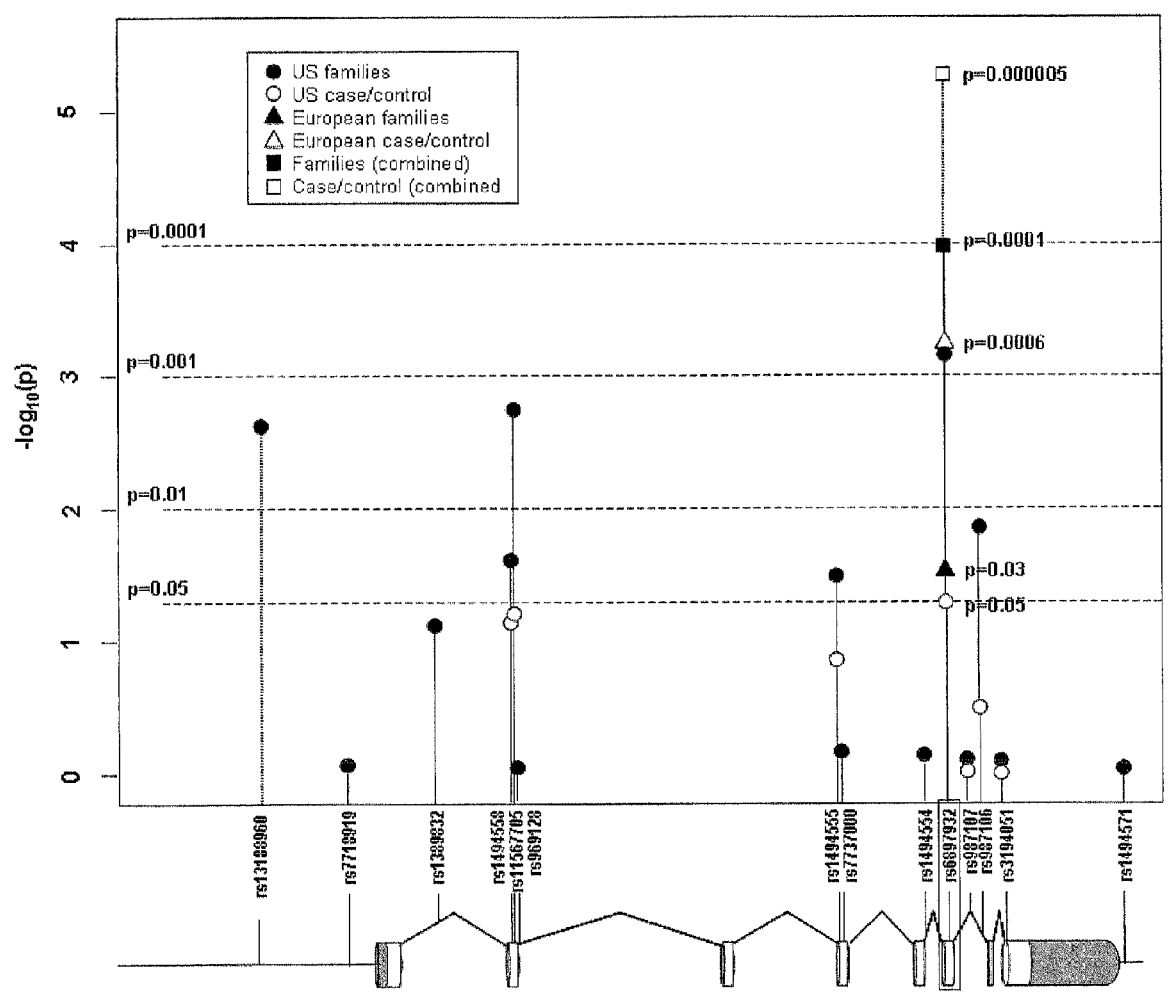
FIG. 1. Physical map and association analysis of single nucleotide polymorphisms (SNPs) from the IL7Rα gene in US (circles), European (triangles) and combined (squares) family-based and case/control datasets. Untranslated regions of IL7Rα are represented by grey squares and exons by white squares. The significant SNP, rs6897932, is boxed FIGS. 2A-C. Transfections and splicing analysis of IL7Rα minigenes. (A) The splicing construct pl-11 and the insertion of IL7Rα genomic sequence to create minigenes pl-11-IL7R382 and pl-11-IL7R172, that contain the 'T' and 'C' alleles of rs6897932, respectively. Location of rs6897932 is shown by an asterisk. CMV indicates the CMV promoter; pA indicates the bovine growth hormone polyadenylation sequence; XbaI and XhoI sites were used for cloning; and the location of T7 and SP6 vector-specific primers is indicated by arrows. U is the 5' exon of pl-11 and D is the 3' exon of pl-11. Sizes of exon 6 and parts of its flanking introns are shown in brackets. (B) The IL7Rα minigenes pl-11-IL7R382 and pl-11-IL7R172 containing the 'T' allele and 'C' allele, respectively, of rs6897932 were stably transfected in triplicates in HeLa, DT3 and AT3 cells. Mature minigene transcripts that either include (In) or skip (Sk) exon 6 produce 326 bp or 232 bp RT-PCR products, respectively. The error bars represent standard deviation. (C) The percentage of exon 6 inclusion is plotted vs. the nucleotide found at the rs6897932 locus. Exon 6 inclusion was also determined using a minigene where the three nucleotides upstream and three nucleotides downstream of the T at SNP rs6897932 were substituted by transversions (mut). The error bars represent standard deviations of triplicate transient transfections. "In" indicates included and "Sk" indicates skipped.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

DEFINITIONS

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "multiple sclerosis" describes a well-characterized neurological disorder caused by demyelination of nerve tissue. The term "multiple sclerosis" or "MS" as used herein includes a disease identified as having a particular art-known status, e.g., relapsing remitting (RRMS), primary progressive (PPMS) and secondary progressive (SPMS), wherein the status of MS as defined according to these and similar terms would be well understood by one of ordinary skill in the art and according to the description provided in the Examples included herewith. RRMS, the most common form, is characterized by onset of symptoms followed by complete or nearly complete remission of the symptoms; with this process repeating itself with variable length and severity. The length of time of symptoms is variable, as is the remission period. PPMS is characterized by onset of symptoms without subsequent remission, although the severity and constellation of symptoms may vary. SPMS is characterized by initial onset similar to RRMS, with progression such that remission of symptoms no longer happens. Symptoms of MS include, but are not limited to, cognitive deficits, motor weakness (often seen as balance and coordination impairment and ataxia), sensory disturbances (mot often pain, numbness, and tingling), and visual disturbances (most often optic neuritis and diplopia).

Also as used herein, "linked" describes a region of a chromosome that is shared more frequently in family members or members of a population affected by a particular disease or disorder, than would be expected or observed by chance, thereby indicating that the gene or genes or other identified marker(s) within the linked chromosome region contain or are associated with an allele that is correlated with the presence of a disease or disorder, or with an increased or decreased risk of the disease or disorder. Once linkage is established, association studies (linkage disequilibrium) can be used to narrow the region of interest or to identify the marker (e.g., allele or haplotype) correlated with the disease or disorder.

Furthermore, as used herein, the term "linkage disequilibrium" or "LD" refers to the occurrence in a population of two linked alleles at a frequency higher or lower than expected on the basis of the allele frequencies of the individual genes. Thus, linkage disequilibrium describes a situation where alleles occur together more often than can be accounted for by chance, which indicates that the two alleles are physically close on a DNA strand.

The term "genetic marker" as used herein refers to a region of a nucleotide sequence (e.g., in a chromosome) that is subject to variability (i.e., the region can be polymorphic for a variety of alleles). For example, a single nucleotide polymorphism (SNP) in a nucleotide sequence is a genetic marker that is polymorphic for two (or in some cases, three or four) alleles. SNPs can be present within a coding sequence of a gene, within noncoding regions of a gene and/or in an intergenic (e.g., intron) region of a gene. A SNP in a coding region in which both allelic forms lead to the same polypeptide sequence is termed synonymous (i.e., a silent mutation) and if a different polypeptide sequence is produced, the alleles of that SNP are non-synonymous. SNPs that are not in protein coding regions can still have effects on gene splicing, transcription factor binding and/or the sequence of the non-coding RNA.

Other examples of genetic markers of this invention can include but are not limited to haplotypes (i.e., combinations of alleles), microsatellites, restriction fragment length polymorphisms (RFLPs), repeats (i.e., duplications), insertions, deletions, etc., as are well known in the art.

In the present invention, the term genetic marker is also used to describe the phenotypic effects of the alleles identified herein as associated with MS; including IL7Rα chain mRNA comprising or lacking exon 6, soluble IL7Rα chain and membrane bound IL7Rα chain as described herein.

An "allele" as used herein refers to one of two or more alternative forms of a nucleotide sequence at a given position (locus) on a chromosome. Usually alleles are nucleotide sequences that make up the coding sequence of a gene, but sometimes the term is used to refer to a nucleotide sequence in a non-coding sequence. An individual's genotype for a given gene is the set of alleles it happens to possess.

Also as used herein, a "haplotype" is a set of SNPs on a single chromatid that are statistically associated. It is thought that these associations, and the identification of a few alleles of a haplotype block, can unambiguously identify most other polymorphic sites in its region. Such information is very valuable for investigating the genetics behind common diseases and is collected by the International HapMap Project. The term "haplotype" is also commonly used to describe the genetic constitution of individuals with respect to one member of a pair of allelic genes; sets of single alleles or closely linked genes that tend to be inherited together.

A subject of this invention is any animal that is susceptible to multiple sclerosis as defined herein and can include, for example, humans, as well as animal models of MS such as mouse and rat models of MS including the experimental autoimmune encephalomyelitis (EAE) mouse. Subjects of this invention can be male or female. A subject may be identified as being at risk of developing MS or as having or suspected of having MS by the clinical features provided herein.

As used herein, "nucleic acids" encompass both RNA and DNA, including cDNA, genomic DNA, mRNA, synthetic (e.g., chemically synthesized) DNA and chimeras of RNA and DNA. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

The term "isolated" can refer to a nucleic acid or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state.

An isolated cell refers to a cell that is separated from other cells and/or tissue components with which it is normally associated in its natural state. For example, an isolated cell is a cell that is part of a cell culture.

The term "oligonucleotide" refers to a nucleic acid sequence of at least about six nucleotides to about 100 nucleotides, for example, about 15 to 30 nucleotides, or about 20 to 25 nucleotides, which can be used, for example, as a primer in a PCR amplification or as a probe in a hybridization assay or in a microarray. Oligonucleotides can be natural or synthetic, e.g., DNA, RNA, modified backbones, etc. Peptide nucleic acids (PNAs) can also be used as probes in the methods of this invention.

The present invention further provides fragments or oligonucleotides of the nucleic acids of this invention, which can be used as primers or probes. Thus, in some embodiments, a fragment or oligonucleotide of this invention is a nucleotide sequence that is at least, for example 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, 750, 800, 850, 900, 1000, 1500, 1750 or 1800 contiguous nucleotides of a nucleic acid of this invention (e.g., the genomic sequence of the IL7Rα chain gene; the coding sequence or mRNA sequence (SEQ ID NO:1) (GenBank Accession No. NM_002185 that encodes the IL7Rα chain protein (SEQ ID NO:2) (GenBank Accession No. NP_002176, with and without exon 6 (SEQ ID NO:3) encoding membrane bound or soluble IL7Rα chain (SEQ ID NO:4), respectively. Such fragments or oligonucleotides can be detectably labeled or modified, for example, to include and/or incorporate a restriction enzyme cleavage site when employed as a primer in an amplification (e.g., PCR) assay.

The present invention is based on the discovery of a correlation between particular genetic markers in the interleukin 7 receptor alpha (IL7Rα) chain gene and multiple sclerosis. Thus, in one aspect, the present invention provides a method of identifying a subject as having an increased risk of developing multiple sclerosis, comprising detecting in the subject the presence of a C allele of the single nucleotide polymorphism rs6897932 of the interleukin 7 receptor alpha chain gene, whereby the presence of said C allele identifies the subject as having an increased risk of developing multiple sclerosis.

Also provided is a method of identifying a subject as having an increased risk of developing multiple sclerosis, comprising testing a nucleic acid sample from the subject (e.g., genotyping the subject) for the presence of a C allele of the single nucleotide polymorphism rs6897932 of the interleukin 7 receptor alpha chain gene, whereby the presence of said C allele identifies the subject as having an increased risk of developing multiple sclerosis.

Additionally provided herein is a method of identifying a subject as having multiple sclerosis, comprising detecting in the subject the presence of a C allele of the single nucleotide polymorphism rs6897932 of the interleukin 7 receptor alpha chain gene, whereby the presence of said C allele identifies the subject as having multiple sclerosis. Any subject could be tested for this to determine a risk of developing MS. The method could also be used in conjunction with other clinical tests, e.g., looking for symptoms of disease in a subject carrying the C allele and/or confirming or facilitating a diagnosis of MS on the basis of clinical symptoms and presence of the C allele in a subject.

Also provided is a method of identifying a subject as having multiple sclerosis, comprising testing a nucleic acid sample from the subject (e.g., genotyping the subject) for the presence of a C allele of the single nucleotide polymorphism rs6897932 of the interleukin 7 receptor alpha chain gene, whereby the presence of said C allele identifies the subject as having multiple sclerosis.

The detection of the C allele at the SNP in the interleukin 7 receptor alpha chain gene identified in the GenBank Database under Accession No. rs6897932, as well as the detection of the T allele at this site or the detection of any allele of this invention, can be carried out according to various protocols standard in the art for identifying nucleotides in a nucleotide sequence, and as described in the Examples section provided herein.

In further embodiments, the present invention provides a method of identifying a subject as having an increased risk of developing multiple sclerosis, comprising detecting an increase in the amount of soluble interleukin 7 receptor alpha chain in the subject relative to the amount of soluble interleukin 7 receptor alpha chain in a control subject, whereby the increase in the amount of soluble interleukin 7 receptor alpha chain identifies the subject as having an increased risk of developing multiple sclerosis.

Also provided herein is a method of measuring the amount of soluble interleukin 7 receptor alpha chain in a subject and/or measuring the amount of membrane bound interleukin 7 receptor alpha chain in a subject to identify the subject as having an increased risk of MS or as having MS, whereby an increase in the amount of soluble interleukin 7 receptor alpha chain in the subject relative to the amount of soluble interleukin 7 receptor alpha chain in a control subject, identifies the subject as having an increased risk of developing multiple sclerosis or as having multiple sclerosis and whereby a decrease in the amount of membrane-bound interleukin 7 receptor alpha chain in the subject relative to the amount of membrane-bound interleukin 7 receptor alpha chain in a control subject, identifies the subject as having an increased risk of developing multiple sclerosis or as having multiple sclerosis.

Further provided herein is a method of identifying a subject as having multiple sclerosis, comprising detecting an increase in the amount of soluble interleukin 7 receptor alpha chain in the subject relative to the amount of soluble interleukin 7 receptor alpha chain in a control subject, whereby the increase in the amount of soluble interleukin 7 receptor alpha chain identifies the subject as having an multiple sclerosis.

Methods to detect the amount of soluble interleukin 7 receptor alpha chain in a subject can be carried out by art-known protocols for detecting and measuring an amount of a soluble protein in a sample from the subject and as described in the Examples section herein.

In yet further embodiments of this invention, a method is provided, of identifying a subject as having an increased risk of developing multiple sclerosis, comprising detecting a decrease in the amount of membrane-bound interleukin 7 receptor alpha chain in the subject relative to the amount of membrane-bound interleukin 7 receptor alpha chain in a control subject, whereby the decrease in the amount of membrane-bound interleukin 7 receptor alpha chain identifies the subject as having an increased risk of developing multiple sclerosis.

Additionally provided herein is a method of identifying a subject as having multiple sclerosis, comprising detecting a decrease in the amount of membrane-bound interleukin 7 receptor alpha chain in the subject relative to the amount of membrane-bound interleukin 7 receptor alpha chain in a control subject, whereby the decrease in the amount of membrane-bound interleukin 7 receptor alpha chain identifies the subject as having multiple sclerosis.

Methods to detect the amount of membrane-bound interleukin 7 receptor alpha chain in a subject can be carried out by art-known protocols for detecting and measuring an amount of a membrane-bound protein in a sample from the subject and as described in the Examples section herein.

The present invention further provides a method of identifying a subject as having an increased risk of developing multiple sclerosis, comprising detecting an increase in the amount of interleukin 7 receptor alpha chain mRNA lacking exon 6 in the subject relative to the amount of interleukin 7 receptor alpha chain mRNA lacking exon 6 in a control subject, whereby the increase in the amount of interleukin 7 receptor alpha chain mRNA lacking exon 6 identifies the subject as having an increased risk of developing multiple sclerosis.

Also provided herein is a method of identifying a subject as having multiple sclerosis, comprising detecting an increase in the amount of interleukin 7 receptor alpha chain mRNA lacking exon 6 in the subject relative to the amount of interleukin 7 receptor alpha chain mRNA lacking exon 6 in a control subject, whereby the increase in the amount of interleukin 7 receptor alpha chain mRNA lacking exon 6 identifies the subject as having multiple sclerosis.

In addition, the present invention provides a method of identifying a subject as having an increased risk of developing multiple sclerosis, comprising detecting a decrease in the amount of interleukin 7 receptor alpha chain mRNA comprising exon 6 in the subject relative to the amount of interleukin 7 receptor alpha chain mRNA comprising exon 6 in a control subject, whereby the decrease in the amount of interleukin 7 receptor alpha chain mRNA comprising exon 6 identifies the subject as having an increased risk of developing multiple sclerosis.

A method is also provided herein of identifying a subject as having multiple sclerosis, comprising detecting a decrease in the amount of interleukin 7 receptor alpha chain mRNA comprising exon 6 in the subject relative to the amount of interleukin 7 receptor alpha chain mRNA comprising exon 6 in a control subject, whereby the decrease in the amount of interleukin 7 receptor alpha chain mRNA comprising exon 6 identifies the subject as having multiple sclerosis.

Further provided herein is a method of measuring the amount of interleukin 7 receptor alpha chain mRNA lacking exon 6 in a subject and/or measuring the amount of interleukin 7 receptor alpha mRNA comprising exon 6 in a subject to identify the subject as having an increased risk of MS or as having MS, whereby an increase in the amount of interleukin 7 receptor alpha chain mRNA lacking exon 6 in the subject relative to the amount of interleukin 7 receptor alpha chain mRNA lacking exon 6 in a control subject, identifies the subject as having an increased risk of developing multiple sclerosis or as having multiple sclerosis and whereby a decrease in the amount of interleukin 7 receptor alpha chain mRNA comprising exon 6 in the subject relative to the amount of interleukin 7 receptor alpha chain mRNA comprising exon 6 in a control subject, identifies the subject as having an increased risk of developing multiple sclerosis or as having multiple sclerosis.

Protocols for detecting and measuring an amount of mRNA in a sample from a subject are well known in the art and are described in the Examples section herein. One of skill in the art would be able to distinguish IL7Rα mRNA comprising exon 6 from IL7Rα mRNA lacking exon 6 and therefore carrying out the steps for the methods described herein would be routine to one or ordinary skill in the art.

Further provided herein is a method of identifying a subject as having an increased risk of developing multiple sclerosis, comprising detecting in the subject the presence, in the interleukin 7 receptor alpha chain gene, of a haplotype comprising the C allele of single nucleotide polymorphism rs6897932, and an allele selected from the group consisting of: a) the C allele of single nucleotide polymorphism rs1494555; b) the T allele of single nucleotide polymorphism rs1494555; c) the C allele of single nucleotide polymorphism rs987107; d) the T allele of single nucleotide polymorphism rs987107; e) the A allele of single nucleotide polymorphism rs987106; f) the T allele of single nucleotide polymorphism rs987106 and g) any combination of (a), (b), (c) (d), (e) and (f), whereby the presence of said haplotype identifies the subject as having an increased risk of developing multiple sclerosis.

Additionally provided herein is a method of identifying a subject as having multiple sclerosis, comprising detecting in the subject the presence, in the interleukin 7 receptor alpha chain gene, of a haplotype comprising the C allele of single nucleotide polymorphism rs6897932, in combination with an allele selected from the group consisting of: a) the C allele of single nucleotide polymorphism rs1494555; b) the T allele of single nucleotide polymorphism rs1494555; c) the C allele of single nucleotide polymorphism rs987107; d) the T allele of single nucleotide polymorphism rs987107; e) the A allele of single nucleotide polymorphism rs987106; f) the T allele of single nucleotide polymorphism rs987106 and g) any combination of (a), (b), (c) (d), (e) and (f), whereby the presence of said haplotype identifies the subject as having multiple sclerosis.

In particular embodiments of the above methods, the haplotype can comprise a) the C allele of single nucleotide polymorphism rs6897932, b) the C allele of single nucleotide polymorphism rs1494555; c) the C allele of single nucleotide polymorphism rs987107; and d) the A allele of single nucleotide polymorphism rs987106.

In other embodiments, the haplotype can comprise: a) the C allele of single nucleotide polymorphism rs6897932, b) the T allele of single nucleotide polymorphism rs1494555; c) the T allele of single nucleotide polymorphism rs987107; and d) the T allele of single nucleotide polymorphism rs987106.

In further embodiments, the haplotype can comprise: a) the C allele of single nucleotide polymorphism rs6897932, b) the T allele of single nucleotide polymorphism rs1494555; c) the C allele of single nucleotide polymorphism rs987107; and d) the A allele of single nucleotide polymorphism rs987106.

Further provided herein is a method identifying a subject as having an increased risk of developing multiple sclerosis or of having multiple sclerosis, comprising testing a nucleic acid sample from the subject (i.e., genotyping the subject) for the presence, in the interleukin 7 receptor alpha chain gene of the subject, of a haplotype comprising the C allele of single nucleotide polymorphism rs6897932, and an allele selected from the group consisting of: a) the C allele of single nucleotide polymorphism rs1494555; b) the T allele of single nucleotide polymorphism rs1494555; c) the C allele of single nucleotide polymorphism rs987107; d) the T allele of single nucleotide polymorphism rs987107; e) the A allele of single nucleotide polymorphism rs987106; f) the T allele of single nucleotide polymorphism rs987106 and g) any combination of (a), (b), (c) (d), (e) and (f), whereby the presence of said haplotype identifies the subject as having an increased risk of developing multiple sclerosis or of having multiple sclerosis.

In certain embodiments, the haplotype of this invention that identifies a subject as having an increased risk of developing MS or as having MS can further comprise the A allele at single nucleotide polymorphism rs3194051.

The present invention further provides a method of identifying a subject as having a decreased risk of developing multiple sclerosis, comprising detecting in the subject the presence of a T allele of the single nucleotide polymorphism rs6897932 of the interleukin 7 receptor alpha chain gene, whereby the presence of said T allele identifies the subject as having a decreased risk of developing multiple sclerosis.

The present invention further provides a method of identifying a subject as having a decreased risk of developing multiple sclerosis, comprising testing a nucleic acid sample of the subject (i.e., genotyping the subject) for the presence of a T allele of the single nucleotide polymorphism rs6897932 of the interleukin 7 receptor alpha chain gene, whereby the presence of said T allele identifies the subject as having a decreased risk of developing multiple sclerosis.

Also provided herein is a method of identifying a subject as having a decreased risk of developing multiple sclerosis, comprising detecting in the subject the presence, in the interleukin 7 receptor alpha chain gene, of a haplotype comprising: a) the T allele of the single nucleotide polymorphism rs6897932; b) the T allele of the single nucleotide polymorphism rs1494555; c) the C allele of the single nucleotide polymorphism rs987107; and d) the T allele of the single nucleotide polymorphism rs987106, whereby the presence of said haplotype identifies the subject as having a decreased risk of developing multiple sclerosis.

The present invention further provides a method of identifying a subject as having a decreased risk of developing multiple sclerosis, comprising testing a nucleic acid sample from the subject for the presence, in the interleukin 7 receptor alpha chain gene, of a haplotype comprising: a) the T allele of the single nucleotide polymorphism rs6897932; b) the T allele of the single nucleotide polymorphism rs1494555; c) the C allele of the single nucleotide polymorphism rs987107; and d) the T allele of the single nucleotide polymorphism rs987106, whereby the presence of said haplotype identifies the subject as having a decreased risk of developing multiple sclerosis.

Furthermore, the present invention provides a method of identifying a subject as having a decreased risk of developing multiple sclerosis, comprising detecting a decrease in the amount of soluble interleukin 7 receptor alpha chain in the subject relative to the amount of soluble interleukin 7 receptor alpha chain in a control subject, whereby the decrease in the amount of soluble interleukin 7 receptor alpha chain identifies the subject as having a decreased risk of developing multiple sclerosis.

Also provided herein is a method of identifying a subject as having a decreased risk of developing multiple sclerosis, comprising detecting an increase in the amount of membrane-bound interleukin 7 receptor alpha chain in the subject relative to the amount of membrane-bound interleukin 7 receptor alpha chain in a control subject, whereby the increase in the amount of membrane-bound interleukin 7 receptor alpha chain identifies the subject as having a decreased risk of developing multiple sclerosis.

Additionally provided herein is a method of measuring the amount of soluble and/or membrane bound interleukin 7 receptor alpha chain in a subject, whereby a decrease in the amount of soluble interleukin 7 receptor alpha chain in the subject relative to the amount of soluble interleukin 7 receptor alpha chain in a control subject, identifies the subject as having a decreased risk of developing multiple sclerosis and whereby an increase in the amount of membrane-bound interleukin 7 receptor alpha chain in the subject relative to the amount of membrane-bound interleukin 7 receptor alpha chain in a control subject, identifies the subject as having a decreased risk of developing multiple sclerosis.

In addition, the present invention provides a method of identifying a subject as having a decreased risk of developing multiple sclerosis, comprising detecting a decrease in the amount of interleukin 7 receptor alpha chain mRNA lacking exon 6 in the subject relative to the amount of interleukin 7 receptor alpha chain mRNA lacking exon 6 in a control subject, whereby the decrease in the amount of interleukin 7 receptor alpha chain mRNA lacking exon 6 identifies the subject as having a decreased risk of developing multiple sclerosis.

A further embodiment of this invention is a method of identifying a subject as having a decreased risk of developing multiple sclerosis, comprising detecting an increase in the amount of interleukin 7 receptor alpha chain mRNA comprising exon 6 in the subject relative to the amount of interleukin 7 receptor alpha chain mRNA comprising exon 6 in a control subject, whereby the increase in the amount of interleukin 7 receptor alpha chain mRNA comprising exon 6 identifies the subject as having a decreased risk of developing multiple sclerosis.

Additionally provided herein is a method of measuring the amount of interleukin 7 receptor alpha chain mRNA lacking exon 6 and/or the amount of interleukin 7 receptor alpha chain mRNA comprising exon 6 in a subject, whereby a decrease in the amount of interleukin 7 receptor alpha chain mRNA lacking exon 6 in the subject relative to the amount of interleukin 7 receptor alpha mRNA lacking exon 6 in a control subject, identifies the subject as having a decreased risk of developing multiple sclerosis and whereby an increase in the amount of interleukin 7 receptor alpha mRNA comprising exon 6 in the subject relative to the amount of interleukin 7 receptor alpha mRNA comprising exon 6 in a control subject, identifies the subject as having a decreased risk of developing multiple sclerosis.

In the methods described herein, the detection of a genetic marker of this invention (e.g., an allele and/or a haplotype) in a subject can be carried out according to methods well known in the art. For example, nucleic acid can be obtained from any suitable sample from the subject that will contain nucleic acid and the nucleic acid can then be prepared and analyzed according to well-established protocols for the presence of genetic markers according to the methods of this invention. In some embodiments, analysis of the nucleic acid can be carried by amplification of the region of interest according to amplification protocols well known in the art (e.g., polymerase chain reaction, ligase chain reaction, strand displacement amplification, transcription-based amplification, self-sustained sequence replication (3SR), Qβ replicase protocols, nucleic acid sequence-based amplification (NASBA), repair chain reaction (RCR) and boomerang DNA amplification (BDA), etc.). The amplification product can then be visualized directly in a gel by staining or the product can be detected by hybridization with a detectable probe. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, and/or by electrophoresis. Thus, the present invention further provides oligonucleotides for use as primers and/or probes for detecting and/or identifying genetic markers according to the methods of this invention.

The genetic markers of this invention are correlated with multiple sclerosis as described herein according to methods well known in the art and as disclosed in the Examples provided herein for correlating genetic markers with various phenotypic traits, including disease states and pathological conditions and levels of risk associated with developing a disease or pathological condition. In general, identifying such correlation involves conducting analyses that establish a statistically significant association and/or a statistically significant correlation between the presence of a genetic marker or a combination of markers and the phenotypic trait in the subject. An analysis that identifies a statistical association (e.g., a significant association) between the marker or combination of markers and the phenotype establishes a correlation between the presence of the marker or combination of markers in a subject and the particular phenotype being analyzed.

In some embodiments of the methods of this invention, particular alleles of the genetic markers are identified as being correlated with multiple sclerosis or with an increased risk of developing multiple sclerosis. Thus, for example, an allele correlated with an increased risk of multiple sclerosis in a subject or with a diagnosis of multiple sclerosis in a subject can be a C allele at SNP rs6897932. Furthermore, any other allele identified to be highly statistically correlated with this allele can be used to identify a subject at increased risk of developing MS, such as, a C allele at SNP rs1494555, a C allele at SNP rs987107, an A allele at SNP rs987106, as well as a haplotype comprising any combination thereof in addition to the C allele at SNP rs6897932.

Furthermore, as described in the Examples section herein, the phenotypic result of the presence of the C allele at SNP rs6897932 is the production of an IL7Rα mRNA lacking exon 6, thereby producing a soluble form of the IL7Rα chain protein. Thus, an increase in either this mRNA lacking exon 6 or in the soluble form of the IL7Rα protein can be used as a parameter to identify a subject having an increased risk of developing MS or of having MS.

The present invention further provides a method of identifying an effective treatment regimen for a subject with MS, comprising correlating the presence of one or more genetic markers of this invention (e.g., the C allele at SNP rs rs6897932) with an effective treatment regimen for MS.

Also provided is a method of identifying an effective treatment regimen for a subject with MS, comprising: a) correlating the presence of one or more genetic markers of this invention in a test subject with MS for whom an effective treatment regimen has been identified; and b) detecting the one or more markers of step (a) in the subject, thereby identifying an effective treatment regimen for the subject.

Further provided is a method of correlating a genetic marker of this invention with an effective treatment regimen for MS, comprising: a) detecting in a subject with MS and for whom an effective treatment regimen has been identified, the presence of one or more genetic markers of this invention; and b) correlating the presence of the one or more genetic markers of step (a) with an effective treatment regimen for MS.

Examples of treatment regimens for MS are well known in the art.

Patients who respond well to particular treatment protocols can be analyzed for specific genetic markers and a correlation can be established according to the methods provided herein. Alternatively, patients who respond poorly to a particular treatment regimen can also be analyzed for particular genetic markers correlated with the poor response. Then, a subject who is a candidate for treatment for MS can be assessed for the presence of the appropriate genetic markers and the most appropriate treatment regimen can be provided.

In some embodiments, the methods of correlating genetic markers with treatment regimens can be carried out using a computer database. Thus the present invention provides a computer-assisted method of identifying a proposed treatment for MS. The method involves the steps of (a) storing a database of biological data for a plurality of patients, the biological data that is being stored including for each of said plurality of patients (i) a treatment type, (ii) at least one genetic marker associated with MS and (iii) at least one disease progression measure for MS from which treatment efficacy can be determined; and then (b) querying the database to determine the dependence on said genetic marker of the effectiveness of a treatment type in treating MS, to thereby identify a proposed treatment as an effective treatment for a subject carrying a genetic marker correlated with MS.

In one embodiment, treatment information for a patient is entered into the database (through any suitable means such as a window or text interface), genetic marker information for that patient is entered into the database, and disease progression information is entered into the database. These steps are then repeated until the desired number of patients has been entered into the database. The database can then queried to determine whether a particular treatment is effective for patients carrying a particular marker, not effective for patients carrying a particular marker, etc. Such querying can be carried out prospectively or retrospectively on the database by any suitable means, but is generally done by statistical analysis in accordance with known techniques, as described herein.

The present invention is more particularly described in the following examples that are intended as illustrative only since numerous modifications and variations therein will be apparent to those skilled in the art.

EXAMPLES

IL7Rα plays an important role in B- and T-cell differentiation and maintenance via IL7 and thymic stromal lymphopoietin (TSLP) signaling pathways. IL7Rα mediates IL7 signaling by dimerizing with the cytokine receptor common γ ($γ_c$) chain to form the IL7 transmembrane receptor. The availability of membrane bound IL7Rα is the limiting factor in the IL7 receptor formation. Alternative splicing of exon 6, which leads to the mutually exclusive production of membrane bound IL7 receptor or of a soluble form of IL7Rα, also regulates IL7 signaling via cellular secretion of the soluble isoform and binding to IL7 in solution (Goodwin et al. (1990) *Cell* 60:941-951).

Functionally, IL7Rα plays an important role in the body's innate (immediate but non-specific) and adaptive (pathogen specific 'memorized') inflammatory and immunological response. IL7 signaling is critical for T cell differentiation of double negative thymocytes (CD4−/CD8−) and plays a role in survival of double positive (CD4+/CD8+) cells after positive selection (Kondo et al. (1997) *Cell* 91:661-672 and Akashi et al. (1997) *Cell* 89:1033-1041). IL7 signaling also modulates peripheral memory or naive T cell homeostasis (Jameson (2002) *Nat. Rev. Immunol.* 2:547-556). Resting T cells express low levels of IL7Rα that allow them to transduce the signal of trace amounts of IL7 to maintain survival and proliferation. In this context, it is believed that IL7 signaling contributes to the maintenance of low affinity T cells in homeostatic peripheral expansion conditions (Fry et al. (2005) *J. Immunol.* 174:6571-6576). Because of the very low levels of IL7Rα expression in T cells, any further decrease in IL7Rα expression or function may have a significant effect on IL7 signaling and T cell regulation and maintenance.

IL7R also plays an important role in the TSLP signaling pathway via dimerization with the cytokine receptor-like factor 2 gene (CRLF2) to form the TSLP receptor (Al Shami et al. (2004) *J. Exp. Med.* 200:159-168). TSLP is an IL7-like cytokine that drives immature B cell development in vitro and, in myeloid dendritic cells, can promote naive CD4+ T cells to differentiate into a T helper type 2 (Th2) phenotype and promote the expansion of CD4+ Th2 memory cells (Huston et al. (2006) *Curr. Allergy Asthma Rep.* 6:372-376). TSLP is thought to trigger dendritic cell-mediated Th2-type inflammatory responses and is considered as a master switch for allergic inflammation (Koyama et al. (2007) *Biochem. Biophys. Res. Commun.* 357:99-104), which is relevant to the etiology of MS.

Candidate gene analyses from two previous studies have suggested a role for IL7Rα in MS. The first study (Teutsch et al. (2003) *Eur. J. Hum. Genet.* 11:509-515) identified a suggestive but not statistically significant effect (p=0.1) of a promoter region haplotype in IL7Rα when only DRB1*1501 positive MS cases were considered. The second study (Zhang et al. (2005) *Genes Immun.* 6:145-152) examined 66 MS candidate genes and found SNPs within IL7Rα to be statistically significant in an MS case-control population, both by single-locus and haplotype analysis. The family-based analysis described herein confirmed the previous result for rs987106 in intron 6 of IL7Rα (p=0.01 in Table 2, p=0.04 in Zhang et al.). However, the most significant non-synonymous coding SNP from the Zhang et al. study, rs3194051 in exon 8 of IL7Rα, was not significant in the present dataset (p=0.79 in Table 2). The most significant polymorphism from this study, rs6897932, was not genotyped in these two previous association studies. The combination of the genetic and molecular data described herein, therefore, indicates that the previously identified association of IL7Rα with MS is being driven by the functional effect of rs6897932.

By using both statistical and functional data, statistical associations were identified between nucleotide variants within the interleukin 7 receptor alpha (IL7Rα) chain gene and MS. A large dataset of US families of European descent (Caucasian) including MS patients were analyzed and a significant association with MS susceptibility was identified only for a non-synonymous coding SNP (rs6897932) within a key transmembrane domain of IL7Rα. This initial significant association was subsequently replicated in three independent European or European descent Caucasian populations including MS patients with unrelated controls and/or their parents from the United States and Northern Europe (United Kingdom and Belgium).

The present studies also demonstrated that rs6897932 affects alternative splicing of exon 6, leading to increased skipping of the exon. This is expected to increase production of soluble IL7Rα for individuals carrying the risk allele at rs6897932. The present studies describe the allelic association of a polymorphism in the IL7Rα gene as a significant risk factor for MS as demonstrated in four independent family-based or case-control datasets.

Example 1

MS and Control Datasets

Four large, independent datasets were used in these studies. Individuals with MS could be classified by disease subtype as relapsing-remitting (RRMS), secondary progressive (SPMS), progressive-relapsing (PRMS) or primary progressive (PPMS). A clinical and demographic description of these patients is shown in Table 1 and the datasets are described in detail below.

The US family dataset consisted of 760 stringently ascertained families of MS patients (563 single-case and 197 multiple-case families), which included 1055 sampled affected individuals (male and female) with MS. All known ancestors were non-Hispanic individuals of European descent. Diagnostic criteria and ascertainment protocols have been summarized elsewhere (e.g., Haines et al. (1996) *Nat. Genet.* 13:469-471; Barcellos et al. (2004) *Ann. Neurol.* 55:793-800). All affected family members were examined or had their medical records reviewed. 83% could be classified by disease subtype, as RRMS, SPMS, PRMS, or PPMS. SPMS was defined by six months of worsening neurological disability not explained by relapse and measured as a deterioration of either: 1) one or more points on the expanded disability status scale (EDSS) in patients with an EDSS less than 6, or 2) a one-half point or more for those with an EDSS>6. PPMS was defined both by 1) progressive clinical worsening for more than 12 months from symptom onset without any relapses, and 2) abnormal cerebrospinal fluid (CSF) as defined by the presence of two or more oligoclonal bands or elevated IgG index in the CSF. If acute relapses were superimposed on this steadily progressive course, patients were considered to have PRMS. The family collection has been ongoing for >20 years and disease subtype information is not available on some of the first MS patients collected (17%). The protocol was approved by the Committee on Human Research at the University of California, San Francisco, and informed consent was obtained from all participants.

The US case-control dataset was ascertained through a prospective study of phenotype-genotype-biomarker associations in a large cohort of MS patients followed longitudinally. MS patients (aged 18 to 65 years) who were evaluated in the Multiple Sclerosis Center at the University of California, San Francisco between July 2004 and September 2005 were invited to participate. This study preferentially recruited patients with a recent onset of MS, although individuals with all clinical subtypes (RRMS, SPMS, PRMS, and PPMS) participated. Therefore, there are more RRMS patients in the case-control dataset, while many RRMS patients in the family-based dataset have progressed to SPMS since the time at which they were first collected. Patients were asked to invite a healthy control of the same sex and ethnicity and similar age range to participate in the study. The protocol was approved by the Committee on Human Research at the University of California, San Francisco, and informed consent was obtained from all participants.

The European family and case-control datasets were from the UK and Belgium. In the UK, trio families (an affected individual and both parents) and unrelated cases were recruited from across the country as part of an ongoing study of genetic susceptibility to MS. In Belgium, trio families and unrelated cases were recruited from the region of Flanders. Diagnostic criteria were identical to those used in the US, except that progressive-relapsing MS was not distinguished from secondary progressive MS. In Belgium, RRMS and SPMS were grouped together as "bout-onset." All individuals gave written informed consent and the study was approved by the Thames Valley Multicentre Research Ethics Committee (UK) and the ethics committee of the University Hospital Gasthuisberg in Leuven (Belgium), respectively. Unrelated UK control samples were obtained from two sources: 479 from the Human Random Control (HRC) DNA panel (derived from blood donors) supplied by the European Collection of Cell Cultures (ECACC) and 2047 from the British 1958 Birth Cohort. Belgian controls (n=199) were hospital staff and patients with non-inflammatory neurological conditions.

Example 2

Statistical Methods

Statistical methods as described herein were used in data analysis.

A small number of SNP genotypes causing unresolvable Mendelian inconsistencies, as identified by the PED-CHECK® software program (O'Connell et al. (1998) *Am. J. Hum. Genet.* 63:259-266), and those implying greater-than-expected recombination rates given the small physical distances between SNPs, as identified by the MERLIN® software program (Abecasis et al. (2002) *Nat. Genet.* 30:97-101), were eliminated from the analysis. From these data, a residual error rate of <0.3% was estimated.

All SNPs were tested for Hardy-Weinberg equilibrium (HWE) in separate samples of unrelated affected and unaffected individuals, using an exact test implemented in the GDA® program (Zaykin et al. (1995) *Genetica* 96:169-178). Measures of linkage disequilibrium (LD) were calculated with the GOLD® software program (Abecasis et al. (2000) *BioInformatics* 16:182-183).

To compare the genotyped SNPs to the currently known common sequence variation in IL7Rα, downloading was done of all SNP genotypes generated by the HapMap project (The International HapMap Consortium (2003) *Nature* 426: 789-796) on the CEU population, requiring a minor allele frequency ≧10% and genotyping efficiency ≧90%. The algorithm implemented in the Tagger® software (de Bakker et al. (2005) *Nat. Genet.* 37, 1217-1223 (2005)) indicated that four haplotype-tagging SNPs were individually or in combinations of up to three SNPs highly correlated with 32 of the 36 variant alleles (89%) identified by the HapMap project, with a mean $r^2$ of 0.944. This suggests that these four SNPs captured the majority of common sequence variation in IL7Rα. Of the 36 variant alleles identified by the HapMap project, four were untaggable with these four SNPs, two were captured with $r^2$=0.65, one with $r^2$=0.54, one with $r^2$=0.38, and the other 28 were perfectly correlated with $r^2$=1.0.

For the family-based datasets, the pedigree disequilibrium test (PDT) (Martin et al. (2000) *Am. J. Hum. Genet.* 67, 146-154) was used for single-locus association testing and the HBAT module of the FBAT package (Horvath et al. (2004) *Genet. Epidemiol.* 26:61-69) was used for haplotype analysis (using the "hbat-e".command line option).

The SNP-specific maximum number of informative discordant sibling pairs in the US dataset was 807 (395 from multiplex and 412 from singleton families), and the maximum number of informative parent-offspring trios in the US dataset was 479 (151 from multiplex and 328 from singleton families).

MS severity scores (MSSS) were calculated as described previously (Schmidt et al. (2006) *Genes Immun.* 7:384-392). Age of onset and MSSS were analyzed with the QTDT® package (Abecasis et al. (2000) *Am. J. Hum. Genet.* 66:279-292), using the Monks-Kaplan test (Monks et al. (2000) *Am. J. Hum. Genet.* 66:576-592).

The case-control datasets were analyzed by logistic regression (SAS Institute, Cary, N.C.), using an additive allele coding of genotypes (0 for homozygous carriers of the major allele, 1 for heterozygous genotypes, 2 for homozygous carriers of the minor allele) as a screening test for all SNPs. The genotype frequencies in MS cases and controls suggested a recessive model for SNP rs6897932 at IL7Rα, which was used for the joint analysis of the US and European datasets (Table 4), for the combined analysis of HLA and IL7Rα (Table 5), and for the power calculations performed with QUANTO® software (Gauderman (2002) *Am. J. Epidemiol.* 155:478-484). The p-values from the logistic regression model were very similar with and without adjustment for age (continuous) and gender (categorical).

Permutation-based association testing and haplotype analysis were performed with the WHAP® program (Sham et al. (2004) *Behav. Genet.* 34:207-214). The method implemented in WHAP uses a weighted maximum-likelihood approach to allow for ambiguity in statistically inferred haplotypes.

Example 3

Identification of Candidate Genes and SNP Selection

A list was compiled of 323 genes that were observed to be differentially expressed in nine gene expression analyses (Ramanathan et al., *J. Neuroimmunol.* 116:213 (2001); Bomprezzi et al., *Hum. Mol. Genet.* 12:2191 (2003); Matejuk et al., *J. Neurosci. Res.* 73:667 (2003); Franzen et al., *Brain Res. Mol. Brain Res.* 115:130 (2003); Mycko et al., *Brain* 126: 1048 (2003); Koike et al., *J. Neuroimmunol.* 139:109 (2003), Lock et al., *Nat. Med.* 8:500 (2002), Ibrahim et al., *Brain* 124:1927 (2001); and Whitney et al., *Ann. Neurol.* 46:425 (1999)0. Genomic convergence (Hauser et al. (2003) *Hum. Mol. Genet.* 12:671-677) was used to identify 28 genes that were differentially expressed in at least two of these nine expression analyses. Studies were then focused on three genes used for SNP selection: IL7Rα gene [MIM: 146661]; matrix metalloproteinase 19 (MMP19) [MIM: 601807]; and chemokine (C-C motif) ligand 2 (CCL2) [MIM: 158105].

SNPselector® software (Xu et al. (2005) *BioInformatics* 21:4181-4186), which incorporates genotype data and LD structure from the HapMap project, was used to identify SNPs within exons, untranslated, and conserved (putative regulatory) regions within these three genes. Genomic DNA was extracted from whole blood using standard procedures. Five common SNPs were genotyped within MMP19, four SNPs within CCL2, and fourteen SNPs within IL7Rα. All SNP genotypes were generated by the TaqMan® allelic discrimination assay (Applied Biosystems Foster City, Calif.) on a 7900HT genotyping platform (Applied Biosystems Foster City, Calif.), using the Assay-on-Demand or Assay-by-Design service from Applied Biosystems (Foster City, Calif.). Duplicate quality control samples were placed both within and across plates and matching genotypes were required for the genotype data to be included in the analysis. Laboratory personnel were blinded to pedigree structure, affection status and location of quality control samples. All SNPs were required to have at least 95% genotyping efficiency, and SNP rs6897932 had 97% efficiency.

Example 4

Single-Locus Analysis of Candidate Gene SNPs in US Families

Single-locus analysis was performed for IL7Rα, CCL2, or MMP19 SNPs in US families. None of the SNPs genotyped in IL7Rα, CCL2, or MMP19 strongly deviated from Hardy-Weinberg equilibrium in a sample of unrelated affected (p>0.04) or unaffected (p>0.10) individuals (p=0.05 for rs6897932 in affecteds).

The IL7Rα SNPs were identified as having the strongest association with MS of the three genes. No statistically significant evidence for association with MS risk was found for SNPs in CCL2 and MMP19 (Table 6), although this does not completely exclude the possibility of a small effect of either gene.

In the 760 US families (Table 1), the strongest association with MS was found for rs6897932 (p=0.0006 by PDT) (Martin et al. (2000) *Am. J. Hum. Genet.* 67:146-154), a non-synonymous coding SNP (T244I) in exon 6 of IL7Rα. This was followed by p=0.002 for rs11567705 and p=0.002 for rs13188960 (Table 2, FIG. 1). The latter SNPs are in strong linkage disequilibrium (LD) with rs6897932 ($r^2$=0.97 for rs11567705, $r^2$=0.95 for rs13188960).

The result for rs6897932 was due to over-transmission of the major allele (C) to offspring affected with MS. The risk allele frequency was similar in MS patients who did or did not carry the MS-associated alleles HLA-DRB1*1501/1503 (0.79 and 0.78), suggesting that the IL7Rα effect on MS susceptibility is independent of the known HLA effect. A QTDT analysis (Monks et al. (2000) *Am. J. Hum. Genet.* 66:576-592 and Abecasis et al. (2000) *Am. J. Hum. Genet.* 66:279-292) showed absence of association between genotypes at rs6897932 and age at onset of MS (p=0.88) or MS severity (p=0.19 for MS severity scores) (Roxburgh et al. (2005) *Neurology* 64:1144-1151 and Schmidt et al. (2006) *Genes Immun.* 7:384-392).

The p-value of 0.0006 for rs6897932 was significant after accounting for multiple comparisons using a Bonferroni correction for the effective number of independent SNPs evaluated across the three genes (Nyholt (2004) *Am. J. Hum. Genet.* 74:765-769). This number was 4 for CCL2 (5 genotyped SNPs), 3 for MMP19 (4 genotyped SNPs) and 8.7 for IL7Rα (14 genotyped SNPs), for an adjusted significance threshold of 0.05/(4+3+8.7)=0.003.

Example 5

Linkage Disequilibrium and Haplotype Analysis of IL7Rα

IL7Rα is located within a block of very high LD, as indicated by all pairwise D' values between SNPs being ≧0.98. To identify common haplotypes and a subset of haplotype-tagging SNPs within IL7Rα, haplotypes of all 14 genotyped SNPs were analyzed for association with MS susceptibility.

Only four common haplotypes (>5% estimated frequency in family founders) were found in this dataset, and a subset of four SNPs (rs1494555, rs6897932, rs987107, rs987106) was sufficient to distinguish between these four common haplotypes. A significant association with MS susceptibility was observed for haplotypes formed by these four tagging SNPs (global p-value 0.0007, Table 3). The association was due to over-transmission of haplotype C-C-C-A (Table 3) to offspring affected with MS (haplotype-specific p=0.006) and under-transmission of haplotype T-T-C-T (Table 3) (haplotype-specific p=0.00005). These two haplotypes are distinguished by the common risk allele (C) at the coding SNP rs6897932 (single-locus p=0.0006), the C allele at rs1494555 (single-locus p=0.03) and the T allele at rs987106 (single-locus p=0.01) (Table 3).

An evaluation of these four haplotype-tagging SNPs on the HapMap data for the European descent (CEU) population showed that the SNPs genotyped in this study capture the majority (89%) of common sequence variation in IL7Rα with a mean $r^2$ of 0.944. Furthermore, the HapMap data also showed that the very strong LD block that spans the IL7Rα gene does not extend to any flanking genes, indicating that the only functional element within the LD block is IL7Rα. No HapMap-genotyped coding SNPs from any of the flanking genes are highly correlated ($r^2$>0.8) with the most strongly associated SNP rs6897932.

Example 6

Replication of the rs6897932 Effect in Independent Datasets

The rs6897932 effect was replicated in three independent datasets. An independent European descent case-control dataset ascertained in the United States (438 cases, 479 controls, Table 1) was genotyped for seven SNPs, including the four haplotype-tagging SNPs in IL7Rα identified by the family-based analysis (Table 4). Analysis by logistic regression, with adjustment for age and gender, demonstrated statistical significance only for rs6897932 (p=0.05). In the subset of 380 unrelated MS patients with available data on carrier status for HLA-DRB1*1501/1503, risk allele frequencies at rs6897932 were similar in carriers and non-carriers of the MS-associated haplotype (0.76 vs. 0.81, p=0.11). Table 5 shows estimated joint odds ratios (ORs) for carriers of HLA-DRB1*1501/1503 and carriers of the C/C genotype at rs6897932, based on 380 MS patients and 428 controls with available data for both loci. In this dataset, the population-attributable risk percent (PAR %) (Bruzzi et al. (1985) *Am. J. Epidemiol.* 122:904-914) was 40.1% for HLA-DRB1*1501/1503 and 16.4% for rs6897932 at IL7Rα, when adjusting for the other factor. The estimated summary PAR % for both loci was 49.6%, less than the sum of the adjusted PAR % estimates since exposures were not mutually exclusive.

Consistent with Wald $\chi^2$ statistics from the logistic regression analysis, permutation-based single-locus tests for the four haplotype-tagging SNPs were only significant for rs6897932 (p=0.01 with the WHAP® software (PC Sham et al. (2004) *Behav. Genet.* 34:207-214). In contrast to the family-based analysis, an omnibus haplotype test based on the four common haplotypes was not significant (p=0.17). However, the same haplotype that was over-transmitted in the families (C-C-C-A) was observed more frequently in cases (35.0%) than controls (31.6%), while the under-transmitted haplotype (T-T-C-T) was observed less frequently in cases (21.8%) than controls (25.8%) (Table 3). These results indicate that rs6897932 is the strongest single-locus effect within IL7Rα and is responsible for the haplotype association observed in the family-based dataset.

Given these findings, further replication efforts were concentrated on rs6897932, which was genotyped in two independent Northern European populations ascertained in the United Kingdom and Belgium (Table 1). The PDT analysis confirmed a significant association with MS risk in 1338 trio families of European MS patients and their parents (p=0.03). Logistic regression analysis of 1077 independent European MS patients and 2725 unrelated controls also replicated the results from the US datasets (p=0.0006). The minor allele frequencies were very similar in US and European MS patients (21.7% and 23.9%, Table 4) and US and European controls (26.5% and 28.3%, Table 4).

A combined analysis of all 2098 families with PDT (p=0.0001) and a combined logistic regression analysis of all 1512 independent MS patients and 3184 unrelated controls (p=0.000005 for additive SNP genotype coding, adjusted for ascertainment site, US vs. Europe) provided strong statistical support for a genuine association of IL7Rα with MS risk (Table 4, FIG. 1). With T/T and C/T genotypes coded as the reference group, the OR for C/C genotypes was 1.29 (95% Cl 1.14 to 1.46, Table 4). For this effect size and a minor allele frequency of 0.72 in controls, a dataset of 980 cases/980 controls is needed to provide 80% power at significance level α=0.05 for replicating the association observed here. Although this effect was not seen in the subset of patients (n=185) with primary progressive MS (p>0.30), the power to detect the OR observed in relapsing-remitting MS is only 25%.

Example 7

Sequence Analysis of IL7Rα

Exon re-sequencing was used to search for additional unknown SNPs within IL7Rα. De novo sequence was generated using 16 phenotypically normal and 16 affected individuals. The de novo SNP identification was carried out by sequencing exons 2, 3, 4, 5, 6, 7, and 8 of IL7Rα in 16 affected individuals (14 RR, 1 PP and 1 PR), 5 unaffected sibs, and 11 parents using an Applied Biosystems 3730 sequencer (Foster City, Calif.) and manufacturer recommended sequencing protocols. Primers were designed to completely incorporate the exons, intron boundaries, and intronic sequence adjacent to each exon. Genomic sequence was generated from exons 2, 3, 4, 5, 6, 7 and 8 and an upstream region (containing putative regulatory elements) of the gene. Although no additional novel sequence polymorphisms were identified within the 64 chromosomes tested, the possibility that a rare variant with an allele frequency of <5% may contribute to the phenotype cannot be discounted.

The associated T244I variation is located in an important trans-membrane domain of IL7Rα. Multi-species sequence alignment of IL7Rα exon 6 in Ensembl® software (Hubbard et al. (2007) *Nucleic Acids Res.* Database issue) shows that the polar threonine is conserved between chimp, macaque, dog, rabbit, elephant, hedgehog, and bull, indicating that there is a level of evolutionary constraint in nucleotide diversity at the location of rs6897932 in the gene.

Example 8

The Effect of rs6897932 on Differential Splicing of IL7Rα

Evidence was found of a functional role for the alternative rs6897932 alleles on the splicing of exon 6 in IL7Rα. The alternative splicing of IL7Rα has potent consequences for the function of the receptor since transcripts that include exon 6 encode a membrane bound IL7Rα while transcripts that skip exon 6 encode a soluble form of the protein (Goodwin et al. (1990) *Cell* 60:941-951).

To test whether the alternate 'C' and 'T' alleles of rs6897932 could affect the inclusion of exon 6, the two allelic versions of exon 6 and the surrounding intronic sequences were cloned into the alternative splicing minigene construct pl-1 (Carstens et al. (1998) *Mol. Cell Biol.* 18:2205-2217). Genomic DNA from two phenotypically normal individuals, who were homozygous for the 'C' or 'T' alleles of rs6897932, was used to PCR amplify exon 6 of IL7Rα. The last 614 nucleotides of intron 5, the entire exon 6 and the first 573 nucleotides of intron 6 of IL7Rα were amplified and cloned between the XbaI and XhoI sites in the splicing reporter minigene pl-11 (Carstens et al. (1998) *Mol. Cell Biol.* 18:2205-2217), to create splicing reporters pl-11-IL7R172 and pl-11-IL7R382.

Mutants of the minigenes were created with either A or G at rs6897932 and a version of pl-11-IL7R382 was also created wherein 3 nucleotides upstream and 3 nucleotides downstream of this locus were mutated (TAA[T]CAT→GCC[T]ACG). All constructs and subclones were sequenced.

Rat DT3 cells were cultured in low glucose DMEM (Invitrogen, Carlsbad, Calif.) with 10% FBS. HeLa cells were cultured in high glucose DMEM with 10% FBS. Stable transfections (FIG. 2B) were as described in Baraniak et al. (*Mol. Cell Biol.* 23:9327-9337 (2003). Transient transfections (FIG. 2C) used the same stable transfection protocol except that 100 ng of DNA was transfected in cells and cells were harvested 48 hours post-transfection without any selection. All transfections were performed in triplicate for each construct. Total RNA was extracted from stable cells using TRIzol® reagent (Invitrogen, Carlsbad, Calif.) according to the manufacturer's protocol and exon 6 inclusion was determined by RT-PCR analysis previously described (Carstens et al. (1998) *Mol. Cell Biol.* 18:2205-2217 and Baraniak et al. (2003) *Mol. Cell Biol.* 23:9327-9337). PCR products were loaded directly on a 5% poly-acrylamide non-denaturing gel, electrophoresed at 100 V for 3 to 4 h and exposed to Amersham Hyperfilm™ MP (GE Healthcare Bio-Sciences Corp. Piscataway, N.J.) or Molecular Dynamics phosphorimager screens (Molecular Dynamics Sunnyvale, Calif.). Quantification of PCR products was performed with ImageQuant® software (Molecular Dynamics, Sunnyvale, Calif.). In each case, RT-PCR products were normalized for molar equivalence.

Figure 2:
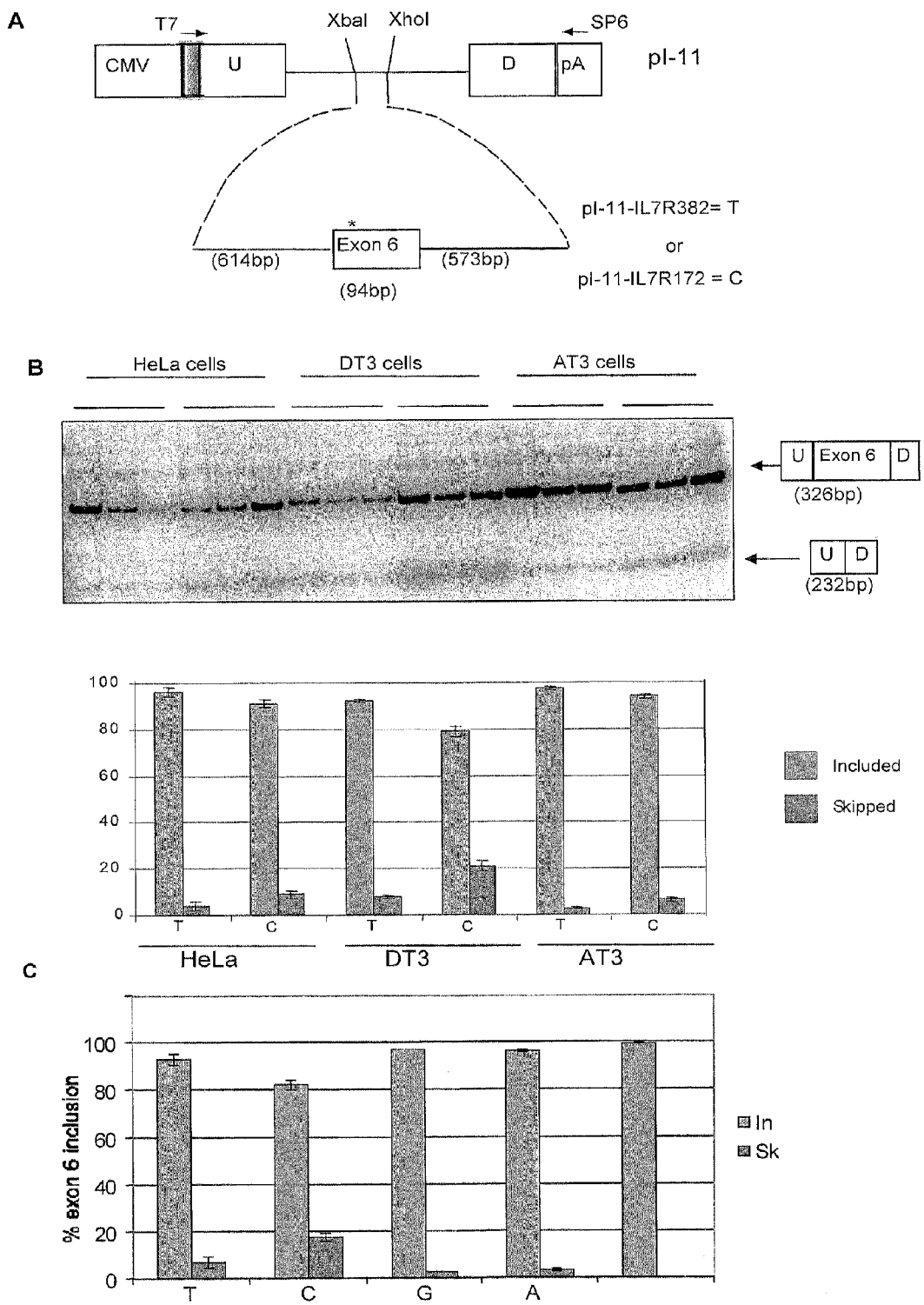

Analysis of transcripts from the two minigenes revealed that the MS-associated 'C' allele resulted in a ~2 fold increase in the skipping of exon 6 compared to the transcripts containing the 'T' allele (FIG. 2). These data are consistent with at least two scenarios: the MS-associated 'C' allele weakens an exonic splicing enhancer (ESE) or it augments an exonic splicing silencer (ESS). The latter is more likely the case since transversions at the rs6897932 locus to either a G or an A nucleotide significantly decreased exon skipping (e.g., production of soluble IL7Rα), and substitutions adjacent to the SNP essentially abolished skipping (FIG. 2). These results are consistent with the presence of a weak ESS that mediates low level of exon 6 skipping resulting in about 10% soluble IL7Rα. These data demonstrate a functional role for the alternative rs6897932 alleles on the splicing of exon 6 in IL7Rα.

Example 9

Allele Specific Expression of IL7Rα

IL7Rα expression was analyzed in healthy controls. Peripheral blood mononuclear cell (PBMC) samples were obtained from 94 healthy controls. Real-time PCR was carried out in 94 control individuals using an Applied Biosystems (Foster City, Calif.) TaqMan® one-step RT-PCR master mix reagents kit under manufacturer's conditions on an ABI 7900HT Sequence Detection System (Applied Biosystems Foster City, Calif.) using SDS 2.0 software. Positive and negative controls, as well as a calibration curve spanning five orders of magnitude constructed with an in vitro transcribed clone of GAPDH, all in triplicate, were also included in each reaction plate. Amplification values are expressed as $10^{12}/2^{ct}$. Three different gene expression TaqMan® assays were tested: Hs00233682_ml, which covers the IL7R exon 4/5 boundary; Hs00904814_ml, which covers the exon 6/7 boundary; and Hs00902338_g1, which covers the exon 7/8 boundary.

The samples were analyzed to detect differential expression of IL7Rα using one amplicon that spanned exons 6-7 and two control amplicons spanning exons 4-5 and exons 7-8, respectively. Using analysis of variance with Bonferroni correction, a statistically significant lower level of expression of the exon 6-7 amplicon was observed for carriers of the MS-associated 'C' allele (p=0.015); the two control amplicons (exons 4-5 and 7-8) had no significantly different expression by genotype. Consistent with in vitro experiments, this indicates that carriers of the 'C' allele at rs6897932 produce less membrane bound IL7Rα protein compared to carriers of the 'T' allele, leading to a further increase of the soluble form of IL7Rα. This is supported by previous findings that interleukin-7 (IL7) functioning and IL7Rα expression in T cells is reduced in MS patients (AL Cox et al. (2005) *Eur. J. Immunol.* 35:3332-3342). These results indicate that the MS-associated "C" risk allele of IL7Rα would likely decrease membrane bound expression of IL7Rα.

Example 10

Differential Expression of IL7Rα Isoforms

Peripheral blood mononuclear cells from six MS patients, who were homozygous TT, heterozygous TC or homozygous CC for SNP rs6897932, were analyzed by semi-quantitative RT-PCR to detect differential expression of IL7Rα isoforms. PCR probes were designed to exons 5 and 7 of IL-7Rα to identify exon 6 inclusion or skipping.

Figure 3:
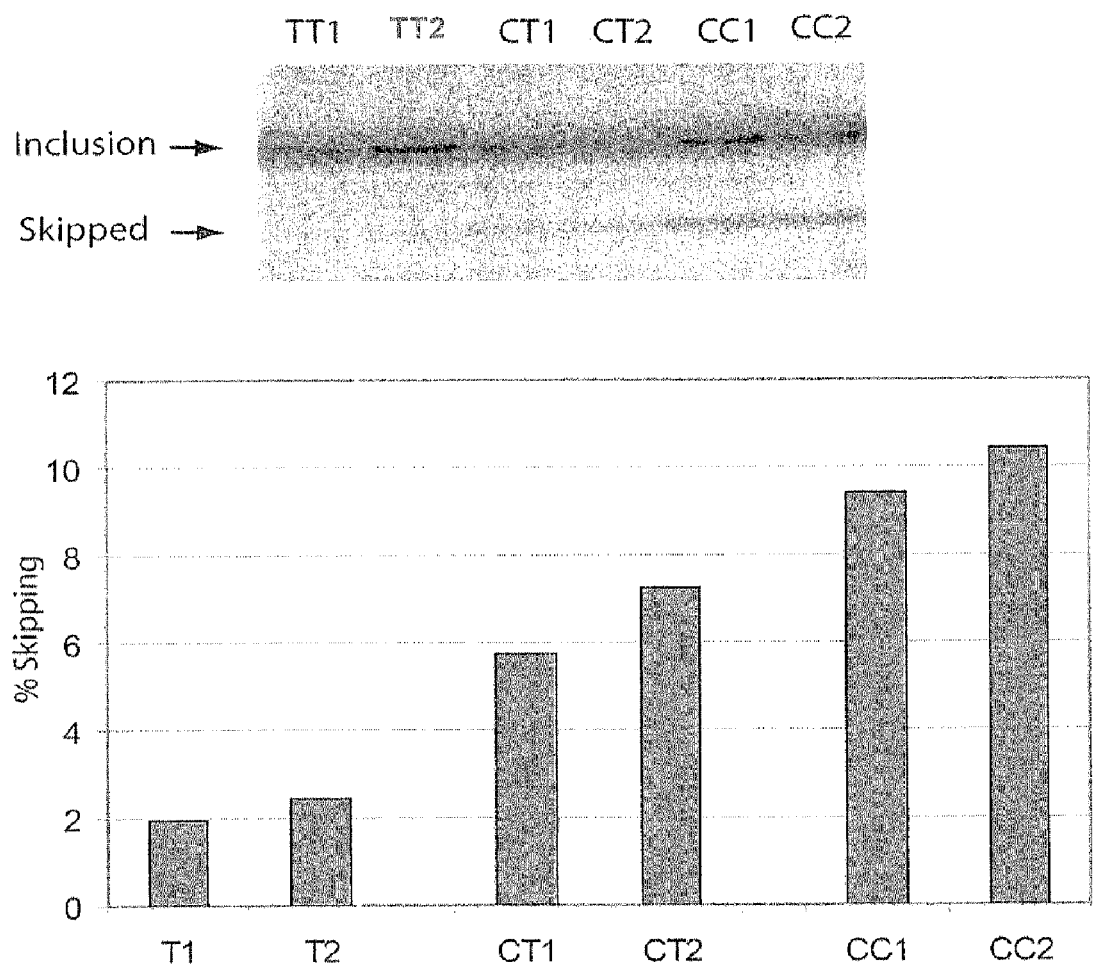
FIG. 3. Differential expression of IL7Rα isoforms in peripheral blood mononuclear cells (PBMCs). PBMCs from six MS patients, who were TT, TC or Cc for SNP rs6897932, were analyzed by semiquantitative RT-PCR to detect differential expression of IL7Rα isoforms. PCR probes were designed to exons 5 and 7 of IL7Rα to identify exon 6 inclusion or skipping. The percentage of the soluble form is in relation to the total IL7Rα mRNA transcription.

The presence of the C allele led to increased skipping of exon 6 (FIG. 3). Levels of soluble IL7Rα mRNA were 4-5 fold higher in the patients homozygous for the C allele relative to those homozygous for the T allele. When compared to the minigene construct endogenous levels of exon 6 skipping within MS patients results in a five fold increase of soluble IL7Rα as compared with the membrane bound receptor in comparison to the two fold difference seen in the in vitro model, although the MS mRNA splicing analysis is assaying transcripts from two alleles assuming that both are expressing IL-7Rα.

The foregoing is illustrative of the present invention, and is not to be construed as limiting thereof. The invention is defined by the following claims, with equivalents of the claims to be included therein. All publications, patent applications, patents, patent publications, sequences identified by Genbank and/or SNP accession numbers, NCBI Build 35 of human chromosome 3 and other references cited herein are incorporated by reference in their entireties for the teachings relevant to the sentence and/or paragraph in which the reference is presented.

TABLE 1

Clinical characteristics of the family-based and case-control MS datasets.

| | US dataset | | | European dataset | | |
|---|---|---|---|---|---|---|
| | MS patients in families (n = 1055) | Cases (n = 438) | Controls (n = 479) | MS patients in families (n = 1338) | Cases (n = 1077) | Controls (n = 2725) |
| Age: Mean (range) in years | | | 41.6 (21-60) | | | 44.6 (24-61) |
| Age at onset: Mean (range) in years | 29.8 (3-63) | 31.9 (11-60) | | 27.1 (9-53) | 33.6 (10-62) | |
| Female: n (%) | 784 (74.3) | 299 (68.3) | 318 (66.4) | 987 (74.0) | 738 (68.5) | 1350 (49.5) |
| Disease type: n (%) | | | | | | |
| relapsing-remitting | 552 (52.3) | 365 (83.3) | — | 1152 (86.1) | 875 (81.2) | — |
| secondary progressive | 260 (24.6) | 54 (12.3) | — | | | — |
| progressive-relapsing | 16 (1.5) | 3 (0.7) | — | NA | NA | — |
| primary progressive | 43 (4.1) | 14 (3.2) | — | 80 (6.0) | 146 (13.6) | — |
| missing | 184 (17.4) | 2 (0.5) | — | 106 (7.9) | 56 (5.2) | — |
| Disease duration: Mean (range) in years | 13.6 (0-50) | 9.9 (0-44) | — | 10.8 (0-39) | 16.4 (0-57) | — |

Family-based US dataset: 760 families (197 with multiple affected relatives (multiplex families), 563 with a single affected individual). Family-based European dataset: 1338 trio families. UK patients from trio families: 64.8% relapsing-remitting, 27.4% secondary progressive. Unrelated UK patients: 45.9% relapsing-remitting, 32.6% secondary progressive. For Belgian patients, relapsing-remitting and secondary progressive MS were grouped together as "bout-onset."

TABLE 2

PDT analysis of IL7Rα SNPs.

| SNP | Position (bp) | Minor/major allele | MAF | Gene Region | Type | Amino acid change | Overall PDT p-value |
|---|---|---|---|---|---|---|---|
| rs13188960 * | 35889076 | T/G | 0.24 | upstream | | | *0.0023* |
| rs7718919 | 35891753 | T/G | 0.13 | upstream | | | 0.8707 |
| rs1389832 * | 35894478 | T/C | 0.34 | intron 1 | | | 0.0804 |
| rs1494558 * | 35896825 | A/G | 0.34 | exon 2 | Non-synon. | I66T | 0.0249 |
| rs11567705 | 35896909 | G/C | 0.24 | intron 2 | | | *0.0018* |
| rs969128 | 35896916 | G/A | 0.13 | intron 2 | | | 0.9343 |
| rs1494555 * | 35906947 | C/T | 0.33 | exon 4 | Non-synon. | V138I | 0.0327 |
| rs7737000 | 35907030 | T/C | 0.13 | exon 4 | Synonymous | H165H | 0.6801 |
| rs1494554 * | 35909629 | C/A | 0.29 | intron 5 | | | 0.7175 |
| rs6897932 * | 35910332 | T/C | 0.24 | exon 6 | Non-synon. | T244I | *0.0006* |
| rs987107 * | 35910984 | T/C | 0.29 | intron 6 | | | 0.7856 |
| rs987106 * | 35911350 | T/A | 0.47 | intron 6 | | | 0.0134 |
| rs3194051 * | 35912031 | G/A | 0.29 | exon8 | Non-synon. | I356V | 0.7856 |
| rs1494571 | 35915844 | C/G | 0.28 | downstream | | | 0.9276 |

P-values meeting Bonferroni-corrected significance threshold and respective risk allele are shown in bold italic. Minor allele frequency (MAF) estimated from genotyped founders. SNPs genotyped by the HapMap project are denoted with an *.

TABLE 3

Haplotype analysis of IL7Rα in 760 Caucasian MS families, using four adjacent SNPs that distinguish all common haplotypes.

| | rs1494555 | rs6897932 | rs987107 | rs987106 | Freq. | Global p-value | No. informative families | Z | Haplotype-specific p-value |
|---|---|---|---|---|---|---|---|---|---|
| Haplotype 1 | C | C | C | A | 0.35 | 0.001 | 284 | 2.99 | 0.003 |
| Haplotype 2 | T | C | T | T | 0.27 | | 264 | 0.05 | 0.96 |
| Haplotype 3 | T | T | C | T | 0.23 | | 245 | −3.98 | 0.00007 |
| Haplotype 4 | T | C | C | A | 0.14 | | 180 | 0.79 | 0.43 |

Haplotype frequencies were estimated from genotyped founders. The number of haplotype-specific informative families indicates how often transmission of haplotypes by heterozygous parents could be inferred. The Z statistic, calculated by the HBAT software using the "hbat -e" command, indicates over- (Z > 0) versus under-transmission (Z < 0) of the respective haplotype.

TABLE 4

Logistic regression analysis of four haplotype-tagging IL7Rα SNPs in 438 MS cases and 479 controls (US dataset).

| SNP | Allele | Freq. in MS cases US (Europe) | Freq. in controls US (Europe) | Geno-type | Freq. in MS cases US (Europe) | Freq. in controls US (Europe) | P-value US | P-value Europe |
|---|---|---|---|---|---|---|---|---|
| rs1494555 | C | 0.349 | 0.312 | CC | 0.105 | 0.082 | 0.14 | — |
| | T | 0.651 | 0.688 | CT | 0.489 | 0.461 | | |
| | | | | TT | 0.406 | 0.457 | | |
| rs6897932 | T | 0.217 (0.238) | 0.265 (0.283) | TT | 0.039 (0.055) | 0.065 (0.083) | 0.05 | 0.0006 |
| | C | 0.783 (0.762) | 0.735 (0.717) | CT | 0.357 (0.368) | 0.401 (0.399) | | |
| | | | | CC | 0.605 (0.577) | 0.534 (0.518) | | |
| rs987107 | T | 0.284 | 0.274 | TT | 0.105 | 0.069 | 0.94 | — |
| | C | 0.716 | 0.726 | CT | 0.358 | 0.408 | | |
| | | | | CC | 0.537 | 0.522 | | |
| rs987106 | T | 0.495 | 0.473 | TT | 0.257 | 0.220 | 0.32 | — |
| | A | 0.505 | 0.527 | AT | 0.477 | 0.505 | | |
| | | | | AA | 0.266 | 0.275 | | |

| | Geno-type | Odds Ratio (95% confidence interval) US | Europe | Combined | P-value** US | Europe | Combined |
|---|---|---|---|---|---|---|---|
| rs6897932 | TT, CT | 1.0 (reference) | 1.0 (reference) | 1.0 (reference) | — | — | — |
| | CC | 1.34 (1.03, 1.74) | 1.24 (1.08, 1.44) | 1.29 (1.14, 1.46) | 0.03 | 0.003 | 0.00008 |

Data fpr rs6897932 includes European cases (n = 1077) and controls (n = 2725).
*additive coding of SNP genotypes,
**recessive coding.

TABLE 5

Estimated joint odds ratios and 95% confidence intervals for carriers of HLA-DRB1*1501/1503 and CC genotypes at rs6897932 in IL7Rα, using US dataset of 380 cases and 428 controls with available data for both loci.

| Genotype at rs6897932 in IL7Rα | Non-carrier of HLA-DRB1*1501/1503 | Carrier of HLA-DRB1*1501/1503 |
|---|---|---|
| TT, CT | 1.0 (reference) | 3.95 (2.87, 5.43) |
| CC | 1.37 (1.02, 1.84) | 5.42 (3.45, 8.51) |

TABLE 6

PDT analysis of CCL2 and MMP19 SNPs.

| SNP | Gene | Chromo-Some | Position (bp) | Minor/major allele | MAF | Gene region | PDT p-value |
|---|---|---|---|---|---|---|---|
| rs1024611 | CCL2 | 17 | 29603901 | C/T | 0.29 | 5' of gene | 0.76 |
| rs3760396 | CCL2 | 17 | 29605554 | G/C | 0.20 | 5' of gene | 0.10 |
| rs2857657 | CCL2 | 17 | 29607245 | G/C | 0.20 | intron 1 | 0.73 |

TABLE 6-continued

PDT analysis of CCL2 and MMP19 SNPs.

| SNP | Gene | Chromo-Some | Position (bp) | Minor/major allele | MAF | Gene region | PDT p-value |
|---|---|---|---|---|---|---|---|
| rs4586 | CCL2 | 17 | 29607382 | T/C | 0.37 | exon 2 (syn) | 0.27 |
| rs13900 | CCL2 | 17 | 29608024 | C/T | 0.29 | 3' UTR | 0.67 |
| rs2242295 | MM19 | 12 | 54518443 | A/G | 0.19 | intron 6 | 0.82 |
| rs2291267 | MM19 | 12 | 54519785 | A/G | 0.04 | exon 5 (syn) | 0.31 |
| rs12815039 | MM19 | 12 | 54521845 | G/C | 0.19 | intron 2 | 0.62 |
| rs2291268 | MM19 | 12 | 54522310 | G/A | 0.08 | intron 2 | 0.55 |

Minor allele frequency (MAF) estimated from genotyped founders.

That which is claimed is:

1. A method of identifying a human subject as having an increased risk of developing relapsing remitting multiple sclerosis, comprising detecting in a nucleic acid sample obtained from the subject the presence of a homozygous C allele of the single nucleotide polymorphism rs6897932 of the interleukin 7 receptor alpha chain gene, whereby the presence of said homozygous C allele identifies the subject as having an increased risk of developing relapsing remitting multiple sclerosis, relative to a human subject lacking said homozygous C allele.

2. The method of claim 1, wherein detecting is carried out by a hybridization reaction.

3. The method of claim 1, wherein detecting is carried out by electrophoresis.

4. The method of claim 1, wherein detecting is carried out by restriction endonuclease digestion analysis.

5. The method of claim 1, wherein detecting is carried out by an amplification reaction.

6. The method of claim 3, wherein the amplification reaction is a polymerase chain reaction.

* * * * *

UNITED STATES PATENT AND TRADEMARK OFFICE
CERTIFICATE OF CORRECTION

PATENT NO. : 8,158,344 B2  
APPLICATION NO. : 12/147171  
DATED : April 17, 2012  
INVENTOR(S) : Haines et al.

Page 1 of 1

It is certified that error appears in the above-identified patent and that said Letters Patent is hereby corrected as shown below:

In the Claims:
Column 38, Claim 6, Line 37: Please correct "claim 3," to read -- claim 5, --

Signed and Sealed this
Twenty-ninth Day of October, 2013

Teresa Stanek Rea
*Deputy Director of the United States Patent and Trademark Office*

SEQUENCE LISTING

<160> NUMBER OF SEQ ID NOS: 4

<210> SEQ ID NO 1
<211> LENGTH: 1809
<212> TYPE: DNA
<213> ORGANISM: Homo sapiens
<220> FEATURE:
<221> NAME/KEY: CDS
<222> LOCATION: (90)..(1466)

<400> SEQUENCE: 1

```
gtcttcctcc ctccctccct tcctcttact ctcattcatt tcatacacac tggctcacac      60
atctactctc tctctctatc tctctcaga atg aca att cta ggt aca act ttt      113
                                 Met Thr Ile Leu Gly Thr Thr Phe
                                  1               5 ggc atg gtt ttt tct tta ctt caa gtc gtt tct gga gaa agt ggc tat      161
Gly Met Val Phe Ser Leu Leu Gln Val Val Ser Gly Glu Ser Gly Tyr
         10                  15                  20 gct caa aat gga gac ttg gaa gat gca gaa ctg gat gac tac tca ttc      209
Ala Gln Asn Gly Asp Leu Glu Asp Ala Glu Leu Asp Asp Tyr Ser Phe
 25                  30                  35                  40 tca tgc tat agc cag ttg gaa gtg aat gga tcg cag cac tca ctg acc      257
Ser Cys Tyr Ser Gln Leu Glu Val Asn Gly Ser Gln His Ser Leu Thr
                 45                  50                  55 tgt gct ttt gag gac cca gat gtc aac atc acc aat ctg gaa ttt gaa      305
Cys Ala Phe Glu Asp Pro Asp Val Asn Ile Thr Asn Leu Glu Phe Glu
             60                  65                  70 ata tgt ggg gcc ctc gtg gag gta aag tgc ctg aat ttc agg aaa cta      353
Ile Cys Gly Ala Leu Val Glu Val Lys Cys Leu Asn Phe Arg Lys Leu
         75                  80                  85 caa gag ata tat ttc atc gag aca aag aaa ttc tta ctg att gga aag      401
Gln Glu Ile Tyr Phe Ile Glu Thr Lys Lys Phe Leu Leu Ile Gly Lys
 90                  95                 100 agc aat ata tgt gtg aag gtt gga gaa aag agt cta acc tgc aaa aaa      449
Ser Asn Ile Cys Val Lys Val Gly Glu Lys Ser Leu Thr Cys Lys Lys
105                 110                 115                 120 ata gac cta acc act ata gtt aaa cct gag gct cct ttt gac ctg agt      497
Ile Asp Leu Thr Thr Ile Val Lys Pro Glu Ala Pro Phe Asp Leu Ser
                125                 130                 135 gtc gtc tat cgg gaa gga gcc aat gac ttt gtg gtg aca ttt aat aca      545
Val Val Tyr Arg Glu Gly Ala Asn Asp Phe Val Val Thr Phe Asn Thr
            140                 145                 150 tca cac ttg caa aag aag tat gta aaa gtt tta atg cac gat gta gct      593
Ser His Leu Gln Lys Lys Tyr Val Lys Val Leu Met His Asp Val Ala
        155                 160                 165
```

```
tac cgc cag gaa aag gat gaa aac aaa tgg acg cat gtg aat tta tcc         641
Tyr Arg Gln Glu Lys Asp Glu Asn Lys Trp Thr His Val Asn Leu Ser
170                 175                 180 agc aca aag ctg aca ctc ctg cag aga aag ctc caa ccg gca gca atg         689
Ser Thr Lys Leu Thr Leu Leu Gln Arg Lys Leu Gln Pro Ala Ala Met
185                 190                 195                 200 tat gag att aaa gtt cga tcc atc cct gat cac tat ttt aaa ggc ttc         737
Tyr Glu Ile Lys Val Arg Ser Ile Pro Asp His Tyr Phe Lys Gly Phe
                205                 210                 215 tgg agt gaa tgg agt cca agt tat tac ttc aga act cca gag atc aat         785
Trp Ser Glu Trp Ser Pro Ser Tyr Tyr Phe Arg Thr Pro Glu Ile Asn
                220                 225                 230 aat agc tca ggg gag atg gat cct atc tta cta acc atc agc att ttg         833
Asn Ser Ser Gly Glu Met Asp Pro Ile Leu Leu Thr Ile Ser Ile Leu
            235                 240                 245 agt ttt ttc tct gtc gct ctg ttg gtc atc ttg gcc tgt gtg tta tgg         881
Ser Phe Phe Ser Val Ala Leu Leu Val Ile Leu Ala Cys Val Leu Trp
        250                 255                 260 aaa aaa agg att aag cct atc gta tgg ccc agt ctc ccc gat cat aag         929
Lys Lys Arg Ile Lys Pro Ile Val Trp Pro Ser Leu Pro Asp His Lys
265                 270                 275                 280 aag act ctg gaa cat ctt tgt aag aaa cca aga aaa aat tta aat gtg         977
Lys Thr Leu Glu His Leu Cys Lys Lys Pro Arg Lys Asn Leu Asn Val
                285                 290                 295 agt ttc aat cct gaa agt ttc ctg gac tgc cag att cat agg gtg gat        1025
Ser Phe Asn Pro Glu Ser Phe Leu Asp Cys Gln Ile His Arg Val Asp
                300                 305                 310 gac att caa gct aga gat gaa gtg gaa ggt ttt ctg caa gat acg ttt        1073
Asp Ile Gln Ala Arg Asp Glu Val Glu Gly Phe Leu Gln Asp Thr Phe
            315                 320                 325 cct cag caa cta gaa gaa tct gag aag cag agg ctt gga ggg gat gtg        1121
Pro Gln Gln Leu Glu Glu Ser Glu Lys Gln Arg Leu Gly Gly Asp Val
        330                 335                 340 cag agc ccc aac tgc cca tct gag gat gta gtc atc act cca gaa agc        1169
Gln Ser Pro Asn Cys Pro Ser Glu Asp Val Val Ile Thr Pro Glu Ser
345                 350                 355                 360 ttt gga aga gat tca tcc ctc aca tgc ctg gct ggg aat gtc agt gca        1217
Phe Gly Arg Asp Ser Ser Leu Thr Cys Leu Ala Gly Asn Val Ser Ala
                365                 370                 375 tgt gac gcc cct att ctc tcc tct tcc agg tcc cta gac tgc agg gag        1265
Cys Asp Ala Pro Ile Leu Ser Ser Ser Arg Ser Leu Asp Cys Arg Glu
                380                 385                 390 agt ggc aag aat ggg cct cat gtg tac cag gac ctc ctg ctt agc ctt        1313
Ser Gly Lys Asn Gly Pro His Val Tyr Gln Asp Leu Leu Leu Ser Leu
            395                 400                 405 ggg act aca aac agc acg ctg ccc cct cca ttt tct ctc caa tct gga        1361
Gly Thr Thr Asn Ser Thr Leu Pro Pro Pro Phe Ser Leu Gln Ser Gly
        410                 415                 420 atc ctg aca ttg aac cca gtt gct cag ggt cag ccc att ctt act tcc        1409
Ile Leu Thr Leu Asn Pro Val Ala Gln Gly Gln Pro Ile Leu Thr Ser
425                 430                 435                 440 ctg gga tca aat caa gaa gaa gca tat gtc acc atg tcc agc ttc tac        1457
Leu Gly Ser Asn Gln Glu Glu Ala Tyr Val Thr Met Ser Ser Phe Tyr
                445                 450                 455 caa aac cag tgaagtgtaa gaaacccaga ctgaacttac cgtgagcgac                 1506
Gln Asn Gln aaagatgatt taaaagggaa gtctagagtt cctagtctcc ctcacagcac agagaagaca      1566
aaattagcaa accccacta cacagtctgc aagattctga acattgctt tgaccactct        1626 tcctgagttc agtggcactc aacatgagtc aagagcatcc tgcttctacc atgtggattt      1686
```

```
ggtcacaagg tttaaggtga cccaatgatt cagctattta aaaaaaaaag aggaaagaat    1746
gaaagagtaa aggaaatgat tgaggagtga ggaaggcagg aagagagcat gagaggaaaa    1806
aaa                                                                  1809
```

```
<210> SEQ ID NO 2
<211> LENGTH: 459
<212> TYPE: PRT
<213> ORGANISM: Homo sapiens

<400> SEQUENCE: 2

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Val Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
    290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350
```

```
Asp Val Val Ile Thr Pro Glu Ser Phe Gly Arg Asp Ser Ser Leu Thr
        355                 360                 365

Cys Leu Ala Gly Asn Val Ser Ala Cys Asp Ala Pro Ile Leu Ser Ser
        370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
                420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn Gln
        450                 455

<210> SEQ ID NO 3
<211> LENGTH: 1715
<212> TYPE: DNA
<213> ORGANISM: Homo sapiens
<220> FEATURE:
<221> NAME/KEY: CDS
<222> LOCATION: (90)..(875)

<400> SEQUENCE: 3
gtcttcctcc ctccctccct tcctcttact ctcattcatt tcatacacac tggctcacac       60
atctactctc tctctctatc tctctcaga atg aca att cta ggt aca act ttt      113
                                 Met Thr Ile Leu Gly Thr Thr Phe
                                   1               5 ggc atg gtt ttt tct tta ctt caa gtc gtt tct gga gaa agt ggc tat      161
Gly Met Val Phe Ser Leu Leu Gln Val Val Ser Gly Glu Ser Gly Tyr
         10                  15                  20 gct caa aat gga gac ttg gaa gat gca gaa ctg gat gac tac tca ttc      209
Ala Gln Asn Gly Asp Leu Glu Asp Ala Glu Leu Asp Asp Tyr Ser Phe
 25                  30                  35                  40 tca tgc tat agc cag ttg gaa gtg aat gga tcg cag cac tca ctg acc      257
Ser Cys Tyr Ser Gln Leu Glu Val Asn Gly Ser Gln His Ser Leu Thr
                 45                  50                  55 tgt gct ttt gag gac cca gat gtc aac atc acc aat ctg gaa ttt gaa      305
Cys Ala Phe Glu Asp Pro Asp Val Asn Ile Thr Asn Leu Glu Phe Glu
             60                  65                  70 ata tgt ggg gcc ctc gtg gag gta aag tgc ctg aat ttc agg aaa cta      353
Ile Cys Gly Ala Leu Val Glu Val Lys Cys Leu Asn Phe Arg Lys Leu
         75                  80                  85 caa gag ata tat ttc atc gag aca aag aaa ttc tta ctg att gga aag      401
Gln Glu Ile Tyr Phe Ile Glu Thr Lys Lys Phe Leu Leu Ile Gly Lys
 90                  95                 100 agc aat ata tgt gtg aag gtt gga gaa aag agt cta acc tgc aaa aaa      449
Ser Asn Ile Cys Val Lys Val Gly Glu Lys Ser Leu Thr Cys Lys Lys
105                 110                 115                 120 ata gac cta acc act ata gtt aaa cct gag gct cct ttt gac ctg agt      497
Ile Asp Leu Thr Thr Ile Val Lys Pro Glu Ala Pro Phe Asp Leu Ser
                125                 130                 135 gtc gtc tat cgg gaa gga gcc aat gac ttt gtg gtg aca ttt aat aca      545
Val Val Tyr Arg Glu Gly Ala Asn Asp Phe Val Val Thr Phe Asn Thr
            140                 145                 150 tca cac ttg caa aag aag tat gta aaa gtt tta atg cac gat gta gct      593
Ser His Leu Gln Lys Lys Tyr Val Lys Val Leu Met His Asp Val Ala
        155                 160                 165 tac cgc cag gaa aag gat gaa aac aaa tgg acg cat gtg aat tta tcc      641
```

-continued

```
                Tyr Arg Gln Glu Lys Asp Glu Asn Lys Trp Thr His Val Asn Leu Ser
                170                 175                 180 agc aca aag ctg aca ctc ctg cag aga aag ctc caa ccg gca gca atg        689
Ser Thr Lys Leu Thr Leu Leu Gln Arg Lys Leu Gln Pro Ala Ala Met
185                 190                 195                 200 tat gag att aaa gtt cga tcc atc cct gat cac tat ttt aaa ggc ttc        737
Tyr Glu Ile Lys Val Arg Ser Ile Pro Asp His Tyr Phe Lys Gly Phe
                205                 210                 215 tgg agt gaa tgg agt cca agt tat tac ttc aga act cca gag atc aat        785
Trp Ser Glu Trp Ser Pro Ser Tyr Tyr Phe Arg Thr Pro Glu Ile Asn
                220                 225                 230 aat agc tca gga tta agc cta tcg tat ggc cca gtc tcc ccg atc ata        833
Asn Ser Ser Gly Leu Ser Leu Ser Tyr Gly Pro Val Ser Pro Ile Ile
                235                 240                 245 aga aga ctc tgg aac atc ttt gta aga aac caa gaa aaa att                875
Arg Arg Leu Trp Asn Ile Phe Val Arg Asn Gln Glu Lys Ile
250                 255                 260 taaatgtgag tttcaatcct gaaagtttcc tggactgcca gattcatagg gtggatgaca      935
ttcaagctag agatgaagtg aaggttttc tgcaagatac gtttcctcag caactagaag      995
aatctgagaa gcagaggctt ggaggggatg tgcagagccc caactgccca tctgaggatg    1055
tagtcatcac tccagaaagc tttggaagag attcatccct cacatgcctg gctgggaatg    1115
tcagtgcatg tgacgcccct attctctcct cttccaggtc cctagactgc agggagagtg    1175
gcaagaatgg gcctcatgtg taccaggacc tcctgcttag ccttgggact acaaacagca    1235
cgctgccccc tccatttct ctccaatctg gaatcctgac attgaaccca gttgctcagg     1295
gtcagcccat tcttacttcc ctgggatcaa atcaagaaga agcatatgtc accatgtcca    1355
gcttctacca aaaccagtga agtgtaagaa acccagactg aacttaccgt gagcgacaaa    1415
gatgatttaa aagggaagtc tagagttcct agtctccctc acagcacaga aagacaaaa    1475 ttagcaaaac cccactacac agtctgcaag attctgaaac attgctttga ccactcttcc    1535
tgagttcagt ggcactcaac atgagtcaag agcatcctgc ttctaccatg tggatttggt    1595
cacaaggttt aaggtgaccc aatgattcag ctatttaaaa aaaaaagagg aaagaatgaa    1655
agagtaaagg aaatgattga ggagtgagga aggcaggaag agagcatgag aggaaaaaaa    1715
```

<210> SEQ ID NO 4
<211> LENGTH: 262
<212> TYPE: PRT
<213> ORGANISM: Homo sapiens

<400> SEQUENCE: 4

```
Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
        50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110
```

-continued

```
Glu Lys Ser Leu Thr Cys Lys Lys Ile Asp Leu Thr Thr Ile Val Lys
        115                 120                 125
Pro Glu Ala Pro Phe Asp Leu Ser Val Val Tyr Arg Glu Gly Ala Asn
        130                 135                 140
Asp Phe Val Val Thr Phe Asn Thr Ser His Leu Gln Lys Lys Tyr Val
145                 150                 155                 160
Lys Val Leu Met His Asp Val Ala Tyr Arg Gln Glu Lys Asp Glu Asn
                165                 170                 175
Lys Trp Thr His Val Asn Leu Ser Ser Thr Lys Leu Thr Leu Leu Gln
                180                 185                 190
Arg Lys Leu Gln Pro Ala Ala Met Tyr Glu Ile Lys Val Arg Ser Ile
        195                 200                 205
Pro Asp His Tyr Phe Lys Gly Phe Trp Ser Glu Trp Ser Pro Ser Tyr
        210                 215                 220
Tyr Phe Arg Thr Pro Glu Ile Asn Asn Ser Ser Gly Leu Ser Leu Ser
225                 230                 235                 240
Tyr Gly Pro Val Ser Pro Ile Ile Arg Arg Leu Trp Asn Ile Phe Val
                245                 250                 255
Arg Asn Gln Glu Lys Ile
                260
```